United States Patent
Hsieh et al.

(10) Patent No.: US 10,912,832 B2
(45) Date of Patent: Feb. 9, 2021

(54) MULTI-DRUG DELIVERY SYSTEM AND USES THEREOF

(71) Applicant: Academia Sinica, Taipei (TW)

(72) Inventors: Patrick C. H. Hsieh, Tainan (TW); Pei-Jung Wu, Taoyuan County (TW); Steve Roffler, Taipei (TW); Bill Cheng, Taipei (TW)

(73) Assignee: ACADEMIA SINICA, Taipei (TW)

( * ) Notice: Subject to any disclaimer, the term of this patent is extended or adjusted under 35 U.S.C. 154(b) by 0 days.

(21) Appl. No.: 16/697,810

(22) Filed: Nov. 27, 2019

(65) Prior Publication Data

US 2020/0108143 A1   Apr. 9, 2020

Related U.S. Application Data

(62) Division of application No. 15/325,346, filed as application No. PCT/US2015/039943 on Jul. 10, 2015, now Pat. No. 10,532,097.

(60) Provisional application No. 62/022,683, filed on Jul. 10, 2014.

(51) Int. Cl.

| | |
|---|---|
| *A61K 39/395* | (2006.01) |
| *C07K 16/44* | (2006.01) |
| *A61K 9/00* | (2006.01) |
| *A61K 47/36* | (2006.01) |
| *A61K 47/42* | (2017.01) |
| *A61K 47/68* | (2017.01) |
| *A61K 47/60* | (2017.01) |
| *A61K 9/06* | (2006.01) |
| *A61K 38/00* | (2006.01) |

(52) U.S. Cl.
CPC ...... *A61K 39/39583* (2013.01); *A61K 9/0019* (2013.01); *A61K 9/0024* (2013.01); *A61K 9/06* (2013.01); *A61K 47/36* (2013.01); *A61K 47/42* (2013.01); *A61K 47/60* (2017.08); *A61K 47/6891* (2017.08); *C07K 16/44* (2013.01); *A61K 38/00* (2013.01)

(58) Field of Classification Search
None
See application file for complete search history.

(56) References Cited

U.S. PATENT DOCUMENTS

| 8,586,073 B2 * | 11/2013 | Drapeau | A61K 45/06 424/426 |
|---|---|---|---|
| 8,853,161 B2 | 10/2014 | Defrees et al. | |
| 10,159,741 B2 * | 12/2018 | Hsieh | A61L 27/20 |
| 2003/0017504 A1 | 1/2003 | Roberts et al. | |
| 2012/0220517 A1 | 8/2012 | Defrees et al. | |
| 2013/0195953 A1 | 8/2013 | Drapeau et al. | |

FOREIGN PATENT DOCUMENTS

WO   WO-2013/063155 A2   5/2013

OTHER PUBLICATIONS

Saija et al., "Influence of different penetration enhancers on in vitro skin permeation and in vivo photoprotective effect of flavonoids," International Journal of Pharmaceuticals, vol. 175, 1998, pp. 85-94, 10 pages.
Fong et al., "Dendritic Cells Injected Via Different Routes Induce Immunity in Cancer Patients," J. Immunol., vol. 166, 2001, 99. 4254-4259, 6 pages.
Seidlits et al., "The effects of hyaluronic acid hydrogels with tunable mechanical properties on neural progenitor cell differentiation," Biomaterials, vol. 31, No. 14, pp. 3930-3940, 11 pages.
Hukshorn et al., "Weekly Subcutaneous Pegylated Recombinant Native Human Leptin (PEG-OB) Administration in Obese Men," The Journal of Clinical Endocrinology and Metabolism, vol. 85, No. 11, 2000, pp. 4003-4009, 7 pages.
Schmedlen et al., "Photocrosslinkable polyvinyl alcohol hydrogels that can be modified with cell adhesion peptides for use in tissue engineering," Biomaterials, vol. 23, 2002, pp. 4325-4332, 8 pages.
Upadhyay et al., "The intracellular drug delivery and anti tumor activity of doxorubicin loaded poly(γ-benzyl L-glutamate)-b-hyaluronan polymersomes," Biomaterials, vol. 31, 2010, pp. 2882-2892, 11 pages.
Su et al., "Sensitive Quantification of PEGylated Compounds by Second-Generation Anti-Poly(ethylene glycol) Monoclonal Antibodies," Bioconjugate Chem., vol. 21, 2010, pp. 1264-1270, 7 pages.
Makadia et al., "Poly Lactic-co-Glycolic Acid (PLGA) as Biodegradable Controlled Drug Delivery Carrier," Polymers (Basel), 2011, pp. 1377-1397, 21 pages.

* cited by examiner

*Primary Examiner* — Agnieszka Boesen

(74) *Attorney, Agent, or Firm* — Muncy, Geissler, Olds & Lowe, P.C.

(57) ABSTRACT

Disclosed herein is a multiple drugs delivery system and its uses in treating diseases. The multiple drugs delivery system includes, an anti-PEG antibody for directing the PEGylated therapeutic to the treatment site; and a hydrogel for retaining the anti-PEG antibody and/or the PEGylated therapeutic at the treatment site for at least 3 days. The hydrogel is selected from the group consisting of hyaluronan (HA) or a derivative of HA, collagen, gelatin, fibronectin, fibrinogen, alginate, chitosan, and a synthetic biocompatible polymer. The anti-PEG antibody and the hydrogel are present in the mixture in a ratio from about 1:1 (v/v) to 1:100 (v/v). At least two dosages of the PEGylated therapeutic, which may be the same or different, are administered to the subject, with each dosage being given at about 1 hour to about 1 week apart. Accordingly, a novel method of treating a subject having cancer or ischemia disease is also provided.

14 Claims, 24 Drawing Sheets

MULTI-DRUG DELIVERY SYSTEM AND USES THEREOF

CROSS REFERENCE TO RELATED APPLICATIONS

This application is a Divisional of co-pending application Ser. No. 15/325,346, filed on Jan. 10, 2017, for which priority is claimed under 35 U.S.C. § 120; which is a 371 of international Application No. PCT/US2015/039943 filed on Jul. 10, 2015; which claims priority of U.S. Provisional Application No. 62/022,683 filed on Jul. 10, 2014 under 35 U.S.C. § 119(e), the entire contents of all of which are hereby incorporated by reference.

BACKGROUND OF THE INVENTION

1. Field of the Invention

The present disclosure relates to a multi-drugs delivery system and its use for treating diseases. Specifically, the present disclosure relates to novel use of an anti-polyethylene glycol (PEG) antibody and a hydrogel in allowing multiple delivery of a PEGylated medicine to a subject for treating diseases that include without limiting, cancer and vascular disease.

2. Description of Related Art

PEGylated therapeutic (i.e., the association of polyethylene glycols (PEG) with a therapeutic agent such as a compound, a peptide or a protein) has become a new way of drug administration system, and among the various advantageous features it may offer, site specific targeting perhaps is the most unique one, if it was used with bi-specific anti-PEG antibody. For example, in the case of a cancer treatment regimen, a PEGylated nanoparticle (e.g., doxorubicin liposome) is injected together with bi-specific antibody (BsAb), with one end of the BsAb recognizing the backbone of the PEG molecule, and the other end of the BsAb recognizing a receptor portion on the tumor cell, allowing the PEGylated nanoparticle to be routed to the tumor cell via the action of the BsAb. However, the anti-PEG antibody is rapidly cleared from the blood circulation after administration, thereby diminishes the therapeutic effect the PEGylated therapeutic might offer.

In view of the foregoing, there exists in this art a need of an agent and a delivery system, in which the lifetime of the anti-PEG antibody in the subject is prolonged so that it may continue directing a PEGylated medicine to its treatment site and allows multiple applications of the PEGylated medicine to be delivered thereto, thereby improves or enhances the therapeutic effects rendered by the PEGylated medicine.

SUMMARY

The present disclosure is based, at least in part, unexpected discovery that a hydrogel such as hyaluronan (HA) may help retain an anti-PEG antibody and/or a PEGylated therapeutic at a target site of a subject, thereby allowing multiple dosages of the PEGylated therapeutic to be administered to the subject in need thereof. In the present study, a mouse hind-limb ischemia model system was used to investigate the effect of hydrogel in retaining the anti-PEG antibody and/or PEGylated therapeutic in the subject for the treatment of cancer or vascular ischemia, and results of this invention suggest that hydrogel or a compound capable of forming a gel-like structure, may be used together with an anti-PEG antibody as an adjuvant to a PEGylated therapeutic (e.g., a PEGylated anti-ischemic agent) for treating a subject in need thereof.

Accordingly, it is the first aspect of the present disclosure to provide a delivery system for delivering multiple dosages of a PEGylated therapeutic to a target site of a subject. The delivery system comprises, an anti-PEG antibody for directing the PEGylated therapeutic to the target site; and a hydrogel for retaining the anti-PEG antibody and/or the PEGylated therapeutic at the target site for at least 3 days; wherein the hydrogel is selected from the group consisting of hyaluronan (HA) or a derivative of HA, collagen, gelatin, fibronectin, fibrinogen, alginate, chitosan, a fibrin glue, and a synthetic biocompatible polymer.

According to some embodiments, the synthetic biocompatible polymer may be poly(glycolic acid) (PGA), poly(lactic acid) (PLA), polyurethane (PU), poly(ε-caprolactone), poly(vinyl alcohol) (PVA), polycyanoacrylate (PCA), polyacrylamide, polymethylmethacrylate, (PMMA), poly(lactide-co-glycolide) (PLGA), poly(trimethylene carbonate) (PTMC), polydimethylsiloxane (PDMS), poly(ethylene-co-vinyl acetate) (PEVA), poly(glycolide-co-caprolactone) (PGCL), or poly(lactide-co-caprolactone) (PLCL).

According to other embodiments, the hydrogel is HA or derivative of HA, in which HA has a molecular weight of about 20 kDa to 2,000 kDa, preferably about 1,500 kDa.

According to further embodiments, the derivative of HA may be any of partial or total esters of hyaluronic acid, adipic dihydrazide-modified hyaluronan, amides of hyaluronan, crosslinked hyaluronic acid, heavy metal salts of hyaluronic acid, sulphated hyaluronic acid, N-sulphated hyaluronic acid, amine-modified hyaluronic acid, diamine-modified hyaluronic acid or hyaluronan composite.

It is the second aspect of the present disclosure to provide a method of administering a PEGylated therapeutic to a target site of a subject in need thereof. The method includes steps of, administering to the subject, a sufficient amount of, a mixture of an anti-PEG antibody and a hydrogel, before, together with or after administering the PEGylated therapeutic;

wherein, the hydrogel is selected from the group consisting of hyaluronan (HA) or a derivative of HA, collagen, gelatin, fibronectin, fibrinogen, alginate, chitosan, a fibrin glue, and a synthetic biocompatible polymer; the anti-PEG antibody and the hydrogel are present in the mixture in a ratio from about 1:1 to 1:100 (v/v); and at least two applications of the PEGylated therapeutic are administered to the subject, with each applications being about 1 hour to 1 week apart.

According to embodiments of the present disclosure, the mixture of the anti-PEG antibody and the hydrogel is administered to a site that is different from that of the PEGylated therapeutic. In some examples, the mixture of the anti-PEG antibody and the hydrogel is administered to the intended target site (e.g., tumor or ischemic area), whereas the PEGylated therapeutic is administered from another site distal from the intended target site, such as from a site on the limb. Further, the mixture of the anti-PEG antibody and the hydrogel may be administered to the subject by direct intramuscular injection, whereas the PEGylated therapeutic is administered to the subject by intravenous injection.

In some embodiments, at least two applications of the PEGylated therapeutic are administered to the subject after the administration of the mixture of anti-PEG antibody and the hydrogel. In other embodiments, at least three applications of the PEGylated therapeutic are administered to the subject.

The anti-PEG antibody may be an IgG or IgM, and preferably, may be a humanized IgG or IgM. According to certain embodiments of the present disclosure, the anti-PEG antibody is an IgM, and the hydrogel is HA or a derivative of HA, in which the HA has a molecular weight of about 20 kDa to 2,000 kDa, more preferably, about 50 kDa to 1,800 kDa; and most preferably, about 1,500 kDa. According to other embodiments, the anti-PEG antibody is an IgG, and the hydrogel is HA or a derivative of HA, in which the HA has a molecular weight of about 20 kDa to 2,000 kDa, more preferably, about 50 kDa to 1,800 kDa; and most preferably, about 1,500 kDa. The derivative of HA may be any of partial or total esters of hyaluronic acid, adipic dihydrazide-modified hyaluronan, amides of hyaluronan, crosslinked hyaluronic acid, heavy metal salts of hyaluronic acid, sulphated hyaluronic acid, N-sulphated hyaluronic acid, amine-modified hyaluronic acid, diamine-modified hyaluronic acid.

According to some embodiments, the anti-PEG antibody and HA or its derivatives are present in the mixture in a ratio from about 1:3 (v/v) to about 1:5 (v/v). In some embodiments, the anti-PEG antibody and HA or its derivatives are present in the mixture at a ratio of about 1:3 (v/v). In certain embodiments, the anti-PEG antibody and HA or its derivatives are present in the mixture at a ratio of about 1:4 (v/v). In still other embodiments, the anti-PEG antibody and HA or its derivatives are present in the mixture at a ratio of about 1:5 (v/v).

The PEGylated therapeutic may be any PEGylated medicament, preferably the PEGylated medicament suitable for treating cancer or ischemia disease, which includes but is not limited to, stroke, myocardial infarction (MI) or limb ischemia. The limb ischemia may be any of chronic limb ischemia, acute or chronic limb ischemia or Buerger's Disease (BD).

Accordingly, it is therefore the third aspect of this disclosure to provide a use of the mixture as described above (i.e., the anti-PEG antibody and the hydrogel) for manufacturing an adjuvant to a PEGylated therapeutic for the treatment of a subject suffering from cancer or ischemia disease.

The mixture of the anti-PEG antibody and hydrogel may be administered to a subject before, together with, and/or after the administration of a PEGylated therapeutic so as to help directing the PEGylated therapeutic to its treatment site, such as the site where tumor or ischemic is located in the subject.

According to embodiments of the present disclosure, the mixture of the anti-PEG antibody and the hydrogel is administered to a site that is different from that of the PEGylated therapeutic. In some examples, the mixture of the anti-PEG antibody and the hydrogel is administered to the intended target site (e.g., tumor or ischemic area), whereas the PEGylated therapeutic is administered from another site distal from the intended target site, such as from a site on the limb. Further, the mixture of the anti-PEG antibody and the hydrogel may be administered to the subject by direct intramuscular injection, whereas the PEGylated therapeutic is administered to the subject by intravenous injection.

The PEGylated therapeutic is preferably administered in at least two independent dosages, such as 2, 3, 4 or 5 dosages, with each dosage being administered about 1 hour to 1 week apart, such as 1, 2, 3, 4, 5, 6, 7, 8, 9, 10, 11, 12, 13, 14, 15, 16, 17, 18, 19, 20, 21, 22, 23, 24 hours apart, or 2, 3, 4, 5, 6, or 7 days apart. In some examples, the PEGylated therapeutic is administered in three independent dosages, with each dosage being 8 hours apart. In other examples, the PEGylated therapeutic is administered in three independent dosages, with each dosage being about 1 week apart. According to some embodiments, the PEGylated therapeutic administered at each dosage may be the same or different PEGylated therapeutics.

The subject may be a mammal, preferably a human. The cancer may be any of breast cancer, cervical cancer, ovary cancer, endometrial cancer, melanoma, uveal melanoma, brain tumor, lung cancer, liver cancer, lymphoma, neuroepithelioma, kidney cancer, bladder cancer, pancreatic cancer, prostate cancer, stomach cancer, colon cancer, uterus cancer, hematopoietic tumors of lymphoid lineage, myeloid leukemia, thyroid cancer, thyroid follicular cancer, myelodysplastic syndrome (MDS), tumor of mesenchymal origin, teratcarcinoma, neuroblastoma, glioma, glioblastoma, keratoacanthomas, analplastic large cell lymphoma, esophageal squamous cell carcinoma, follicular dentritic cell carcinoma, intestinal cancer, muscle invasive cancer, seminal vesicle tumor, epidermal carcinoma, spleen cancer, head and neck cancer, stomach cancer, bone cancer, cancer of retina, biliary cancer, small bowel cancer, salivary gland cancer, uterine sarcoma, cancer of testicles, cancer of connective tissue, prostatic hypertrophy, myelodysplasia, Waldenstrom's macroglobulinemia, nasopharyngeal, neuroendocrine cancer, mesothelioma, angiosarcoma, Kaposi's sarcoma, oesophagogastric, fallopian tube cancer, peritoneal cancer, papillary serous mullerian cancer, malignant ascites, gastrointestinal stromal tumor (GIST), Li-Fraumeni syndrome or Von Hippel-Lindau syndrome (VHL).

The hematopoietic tumors of lymphoid lineage may be any of leukemia, acute lymphocytic leukemia, chronic lymphocytic leukemia, B-cell lymphoma, Burkitt's lymphoma, multiple myeloma, Hodgkin's lymphoma, or Non-Hodgkin's lymphoma. The myeloid leukemia may be acute myelogenous leukemia (AML) or chronic myelogenous leukemia (CML). The tumor of mesenchymal origin is fibrosarcomas or rhabdomyosarcomas.

The ischemia disease may be stroke, myocardial infarction (MI), or limb ischemia. The limb ischemia may be any of chronic limb ischemia, acute or chronic limb ischemia or Buerger's Disease (BD).

Accordingly, it is the fourth aspect of this disclosure to provide a method of treating a subject suffering from cancer or ischemia disease by administering to the subject a sufficient amount of the mixture of the anti-PEG antibody and the hydrogel described above; along with an effective amount of a PEGylated therapeutic; so as to ameliorate one or more symptoms related to cancer or ischemia disease. In some embodiments, the effective amount of the PEGylated therapeutic is administered in two independent dosages. In other embodiments, the effective amount of the PEGylated therapeutic is administered in three independent dosages.

The details of one or more embodiments of the invention are set forth in the accompanying description below. Other features and advantages of the invention will be apparent from the detail descriptions, and from claims.

BRIEF DESCRIPTION OF THE DRAWINGS

The present description will be better understood from the following detailed description read in light of the accompanying drawings, where:

FIG. 1(A) The binding profile of PEGylated compounds to the wells coated with AGP4 antibodies. FIG. 1(B) The binding efficiency of PEG-Qd800 to AGP4 in comparison to its binding to IgM, and the binding of Lipo-DOX to AGP4. (P<0.005, *P<0.001 vs. normal IgM-treated)

FIG. 2(A) A schematic diagram illustrating the location at which the subcutaneous and intravenous injection took place. FIG. 2(B) The fluorescence signals of HA/AGP4, and FIG. 2(C) PEG-Qd800 were quantified. The organs on the $1^{st}$, $4^{th}$ and $7^{th}$ day were removed after one administration of both HA/AGP4 and PEG-Qd800, and were subjected to FIG. 2(D) fluorescence intensity measurements. FIG. 2(E) the intravital images were recorded in 1.5 and 4 hours after one subcutaneous administration of HA/AGP4 or HA alone into ear model and one intravenous injection of PEG-Qd655. FIG. 2(F) The fluorescence intensity of PEG-Qd655 was quantified. (*P<0.01, P<0.005, *P<0.001 vs. HA alone-treated)

FIG. 3(A) A schematic diagram depicting the location at which the intramuscular and intravenous injection took place. The fluorescence signals of HA/AGP4 and PEG-Qd800 in the isolated muscle tissues from either legs, in which only the right leg muscle was injected with HA/AGP4 (AGP4 leg). The results were presented in quantitated format as shown in FIG. 3(B). The quantified results of PEG-Qd800 in different organs were depicted in FIG. 3(C). FIG. 3(D) The immunofluorescence staining results and FIG. 3(E) the quantification of fluorescence intensity of PEG-Qd800 after 7 days of different injections of PEG-Qd800 (red) and the skeletal muscle fiber were labeled by Tropomyosin (green) and the nuclei were stained with DAPI (blue). Scale bar: 20 µm. (***P<0.001 vs. 1 injection or vs. normal leg)

FIG. 4(A) A schematic diagram showing the time point and the location at which the injections took place. FIG. 4(B) The immunofluorescence staining results and FIG. 4(C) the quantification of treatments of HA alone+PEGylated IGF-1, HA/AGP4+PBS or HA/AGP4+ PEGylated IGF-1 continuously after HLI surgery. The apoptotic cells were stained by TUNEL staining (red), the membrane lectins were labeled with WGA (green), and the nuclei with stained with DAPI (blue). (*P<0.01; P<0.005; *P<0.001 vs. HA alone+PEGylated IGF-1 or HA/AGP4+ PBS).

FIG. 5(A) A schematic diagram showing the timepoint and the location at which the injections took place. FIG. 5(B) The immunofluorescence staining results and FIG. 5(C) the quantification of treatments of HA/AGP4 followed with PEGylated G-CSF or PBS or HA alone followed with PEGylated G-CSF continuously after HLI surgery. The recruited cells were labeled with anti-CD34 (red) and anti-CD133 (green), and the nuclei with stained with DAPI (blue). (*P<0.01; P<0.005; *P<0.001 vs. HA alone+ PEGylated G-CSF, HA/AGP4+PBS)

FIG. 6(A) A schematic diagram showing the timepoint and the location at which the injections took place. FIG. 6(B) The blood flow at days 0, 1, 3, 7, 14, 21, and 28 in each experimental group was measured by Laser Doppler Flowmetry. FIG. 6(C) The clinical scores of mice 3 to 28 days after the induction of hindlimb ischemia FIG. 6(D) The immunofluorescence staining results of treatments of combined therapies or PBS continuously after HLI surgery. The capillaries were labeled with anti-isolectin (red), the skeletal muscles were labeled with anti-tropomyosin (green), and the nuclei with stained with DAPI (blue). FIG. 6(E) The quantification of the capillary density at the peri-injury region. (*P<0.01; P<0.005; *P<0.001 vs. PBS-treated)

DESCRIPTION

Figure 1A:
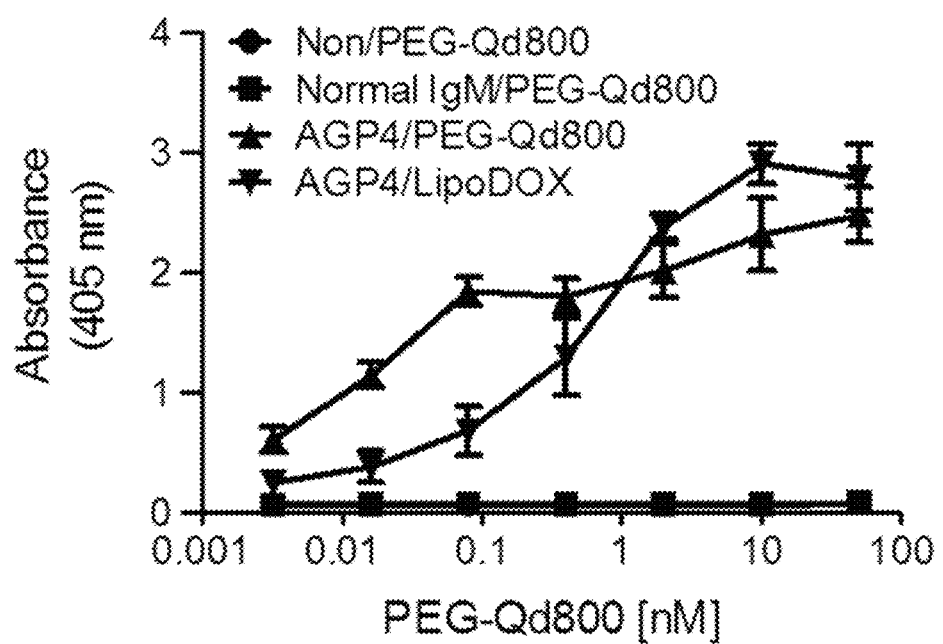
FIGS. 1A-1B: The anti-PEG antibody, AGP4, binds specifically to PEGylated compounds.

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

1. DEFINITIONS

For convenience, certain terms employed in the context of the present disclosure are collected here. Unless defined otherwise, all technical and scientific terms used herein have the same meaning as commonly understood by one of the ordinary skill in the art to which this invention belongs.

The singular forms "a", "and", and "the" are used herein to include plural referents unless the context clearly dictates otherwise.

The term "treatment" as used herein are intended to mean obtaining a desired pharmacological and/or physiologic effect, e.g., inhibiting cancer growth or ameliorating ischemic injury to an organ (e.g., heart). The effect may be prophylactic in terms of completely or partially preventing a disease or symptom thereof and/or therapeutic in terms of a partial or complete cure for a disease and/or adverse effect attributable to the disease. "Treatment" as used herein includes preventative (e.g., prophylactic), curative or palliative treatment of a disease in a mammal, particularly human; and includes: (1) preventative (e.g., prophylactic), curative or palliative treatment of a disease or condition (e.g., a cancer or ischemia disease) from occurring in an individual who may be pre-disposed to the disease but has not yet been diagnosed as having it; (2) inhibiting a disease (e.g., by arresting its development); or (3) relieving a disease (e.g., reducing symptoms associated with the disease).

The terms "PEGylated" compounds, therapeutics and/or medicines as used herein refer to compounds, therapeutics and/or medicines, in which long stands of polyethylene glycol (PEG) polymers are attached thereto. PEGylated compounds, therapeutics and/or medicines typically are peptides, proteins, antibodies, nanoparticles (e.g., liposomes) and etc.

The term "anti-PEG antibody" as used herein refers to an antibody, particularly a monoclonal antibody that is raised against polyethylene glycol (PEG) molecule, meaning the antibody may bind to repeating subunits of the PEG backbone, thus can help quantifying a PEGylated compound (e.g., a PEGylated anti-cancer drug or a PEGylated anti-ischemic medicine). The anti-PEG antibody of the present disclosure may be an IgG or an IgM, and preferably is a humanized IgG or IgM. The anti-PEG antibody of the present disclosure may be produced by any known method, preferably, by procedures previously described by Su et al. (Bioconjugate Chemistry (2010) 21, 1264-1270.)

The term "administered", "administering" or "administration" are used interchangeably herein to refer a mode of delivery, including, without limitation, oral, nasal, pulmonary, transdermal, such as passive or iontophoretic delivery, or parenteral, e.g., rectal, depot, subcutaneous, intravenous, intramuscular, intraperitoneally, intraarterially, intra-cerebella, ophthalmic solution or an ointment. In one embodiment of the present disclosure, the mixture of an anti-PEG antibody and the hydrogel is administered to the subject by direct intramuscular injection, whereas a PEGylated medicine is administered to the subject by direct intraveneous injection.

The term "an effective amount" as used herein refers to an amount effective, at dosages, and for periods of time necessary, to achieve the desired result with respect to the treatment of a disease. For example, in the treatment of a cancer, an agent (i.e., a compound or a composition) which decrease, prevents, delays or suppresses or arrests any symptoms of the cancer would be effective. An effective amount of an agent is not required to cure a disease or condition but will provide a treatment for a disease or condition such that the onset of the disease or condition is delayed, hindered or prevented, or the disease or condition symptoms are ameliorated. The effective amount may be divided into one, two or more doses in a suitable form to be administered at one, two or more times throughout a designated time period.

The term "a sufficient amount" as used herein refers to an amount suffice at dosages, and for periods of time necessary, to achieve the desired result with respect to prolong the in vivo life time of a component of a treatment regimen (e.g., an anti-PEG antibody) so that it is continuously present for a sufficient period of time to help direct the active agent of the treatment regimen (e.g., a PEGylated medicament) toward its target site or the site in the subject in need of the treatment (e.g., the tumor site or the ischemic area). In preferred examples, a sufficient amount of a mixture of anti-PEG antibody and hydrogel is administered to a subject suffering from a disease (e.g., cancer or ischemia disease) treatable by a PEGylated medicament (e.g., a PEGylated anti-cancer drug or a PEGylated anti-ischemia medicine), in which the anti-PEG antibody continued to be present in the subject at least 3 days post a single injection.

The term "adjuvant" as used herein refers to an agent that does not produce therapeutic effect by itself but help routing a therapeutic agent to its intended target site or the treatment site (e.g., an ischemic area or a tumor) of a subject. According to preferred embodiments of the present disclosure, a mixture of an anti-PEG antibody and hydrogel acts as an adjuvant to a PEGylated medicament (e.g., a PEGylated anti-cancer drug or a PEGylated anti-ischemic medicine) for treating a subject in need thereof.

The term "subject" or "patient" refers to an animal including the human species that is treatable with the method of the present invention. The term "subject" or "patient" intended to refer to both the male and female gender unless one gender is specifically indicated. Accordingly, the term "subject" or "patient" comprises any mammal which may benefit from the treatment method of the present disclosure.

The term "cancer" as used herein is intended to mean any cellular malignancy whose unique trait is the loss of normal controls that results in unregulated growth, lack of differentiation and ability to invade local tissues and metastasize. Cancer can develop in any organ or tissue, and may be any of breast cancer, cervical cancer, ovary cancer, endometrial cancer, melanoma, uveal melanoma, brain tumor, lung cancer, liver cancer, lymphoma, neuroepithelioma, kidney cancer, bladder cancer, pancreatic cancer, prostate cancer, stomach cancer, colon cancer, uterus cancer, hematopoietic tumors of lymphoid lineage, myeloid leukemia, thyroid cancer, thyroid follicular cancer, myelodysplastic syndrome (MDS), tumor of mesenchymal origin, teratcarcinoma, neuroblastoma, glioma, glioblastoma, keratoacanthomas, anaplastic large cell lymphoma, esophageal squamous cell carcinoma, follicular dentritic cell carcinoma, intestinal cancer, muscle invasive cancer, seminal vesicle tumor, epidermal carcinoma, spleen cancer, head and neck cancer, stomach cancer, bone cancer, cancer of retina, biliary cancer, small bowel cancer, salivary gland cancer, uterine sarcoma, cancer of testicles, cancer of connective tissue, prostatic hypertrophy, myelodysplasia, Waldenstrom's macroglobulinemia, nasopharyngeal, neuroendocrine cancer, mesothelioma, angiosarcoma, Kaposi's sarcoma, oesophagogastric, fallopian tube cancer, peritoneal cancer, papillary serous mullerian cancer, malignant ascites, gastrointestinal stromal tumor (GIST), Li-Fraumeni syndrome or Von Hippel-Lindau syndrome (VHL). The hematopoietic tumors of lymphoid lineage may be any of leukemia, acute lymphocytic leukemia, chronic lymphocytic leukemia, B-cell lymphoma, Burkitt's lymphoma, multiple myeloma, Hodgkin's lymphoma, or Non-Hodgkin's lymphoma. The myeloid leukemia may be acute myelogenous leukemia (AML) or chronic myelogenous leukemia (CML). The tumor of mesenchymal origin is fibrosarcomas or rhabdomyosarcomas.

The term "ischemic disease" as used herein intended to mean a condition characterized by reduced blood supply of an area such as the heart, the limb or the brain, usually due to blockage of arteries. Exemplary ischemic disease include, without limiting, stroke, myocardial infarction (MI) and limb ischemia. The term "limb ischemia" refers to a condition that affects the blood flow in the limb of a subject, such as chronic limb ischemia (CLI), which progresses into critical limb ischemia leading to the distal limb at risk of amputation, and acute limb ischemia, with a rapid loss of blood flow damaging tissue within hours. Critical limb ischemia is often associated with diabetes, resulting in compromised vasculature and exaggerated tissue damage. A separate chronic condition, Buerger's Disease (BD), would compromise blood flow to the hands and feet resulting in the loss of fingers and toes. Limb ischemia such as CLI or BD generally results in poor wound healing, ulcers and tissue necrosis in limbs and extremities that may result in loss of the affected limb as a result of non-traumatic amputation.

2. DETAIL DESCRIPTION OF PREFERRED EMBODIMENTS

The present disclosure is based, at least in part, unexpected discovery that the hydrogel, is capable of retaining an anti-polyethylene glycol (PEG) antibody and/or a PEGylated therapeutic in a target site of a subject for at least 3 days, thereby allowing multiple applications of the PEGylated therapeutic to be administered to the subject in need of a treatment thereof. The continuous presence of the anti-PEG antibody in the subject not only allows multiple dosage of the PEGylated therapeutic to be applied to the subject, but also help directing the PEGylated therapeutic to its target site (i.e., the site in need of the treatment), as a result, an improved therapeutic effect is achieved, as compared to that of a single application of a PEGylated therapeutic in conventional treatment regimen.

Accordingly, one aspect of the present disclosure is to provide a method of administering a PEGylated therapeutic to a subject in need thereof. The method comprises the step of, administering to the subject, a sufficient amount of, a mixture of an anti-PEG antibody and a hydrogel, before, together with or after administering the PEGylated therapeutic; wherein the anti-PEG antibody and the hydrogel are present in the mixture in a ratio from about 1:1 to 1:100 (v/v), the hydrogel is selected from the group consisting of, hyaluronan (HA) or a derivative of HA, collagen, gelatin, fibronectin, fibrinogen, alginate, chitosan, a fibrin glue made of fibrinogen and thrombin, and a synthetic biocompatible polymer; and at least two applications of the PEGylated therapeutic are administered to the subject, with each application being about 1 hour to 1 week apart.

According to preferred embodiments, the hydrogel is of nature origin, such as HA or a derivative of HA. HA is also known as hyaluronic acid, is an anionic, non-sulfated glycosaminoglycan consisting of repeating disaccharide units of N-acetylglucosamine and D-glucuronic acid. HA is an essential component of the extracellular matrix and considered to be an immuno-neutral polysaccharide; hence, it has been widely used in biomedical applications for decades. Different numbers of the disaccharide subunit result in various molecular weights of HA, ranging from 20 kDa to 2,000 kDa; preferably, from 50 kDa to 1,800 kDa; and more preferably, from 100 kDa to 1,700 kDa. In one preferred embodiment of the present disclosure, HA or a derivative thereof has a molecular weight of about 1,500 kDa.

Derivatives of hyaluronic acid include, but are not limited to, partial or total esters of hyaluronic acid, adipic dihydrazide-modified hyaluronan, amides of hyaluronan, crosslinked hyaluronic acid, heavy metal salts of hyaluronic acid, sulphated hyaluronic acid, N-sulphated hyaluronic acid, amine-modified hyaluronic acid, diamine-modified hyaluronic acid, and hyaluronan composites such as composites of hyaluronan and silk, and hyaluronic acids cross-linked with other natural or synthetic materials. Derivatives of hyaluronic acid can be obtained by chemically modifying one or more functional groups (e.g., carboxylic acid group, hydroxyl group, reducing end group, N-acetyl group) of hyaluronic acid and/or crosslinking hyaluronan with other molecules using methods known in the art.

In some examples, the hydrogel is the fibrin glue, which is made up of fibrinogen and thrombin, in which the thrombin is known to convert the fibrinogen therein into fibrin monomers in a relatively short period of time (e.g., 10 to 60 secs), and thereby give rise to a three-dimensional gel like structure.

According to other embodiments, the hydrogel is of synthetic origin, such as the synthetic biocompatible polymer, which may be selected from the group consisting of, poly(glycolic acid) (PGA), poly(lactic acid) (PLA), polyurethane (PU), poly(ε-caprolactone) (PCL), poly(vinyl alcohol) (PVA), polycyanoacrylate (PCA), polyacrylamide, polymethylmethacrylate, (PMMA), poly(lactide-co-glycolide) (PLGA), poly(trimethylene carbonate) (PTMC), polydimethylsiloxane (PDMS), poly(ethylene-co-viny; acetate) (PEVA), poly(glycolide-co-caprolactone) (PGCL), and poly(lactide-co-caprolactone) (PLCL).

Hydrogel may help prolong the circulation of an anti-PEG antibody in a subject by preventing the anti-PEG antibody from being rapidly metabolized, thus may retain the anti-PEG antibody and in turn, the PEGylated medicine, in the treatment site for a longer period. According to embodiments of the present disclosure, the anti-PEG antibody is encapsulated within the gel-like structure of the hydrogel (such as HA), thus prolongs the life-time of the anti-PEG antibody for at least 3 days, such as 3, 4, 5, 6 or 7 days, in the subject. Due to the prolong existence of the anti-PEG antibody in the subject, multiple dosages (e.g., 2, 3, 4, 5 or 6 dosages), instead of a single dosage, of a PEGylated medicine, may be administered to the subject, thereby results in an improved therapeutic effect in the subject. In some examples, at least 2 dosages of the PEGylated medicine are administered. In other examples, at least 3 dosages of the PEGylated medicine are administered. Each dosage of the PEGylated medicine is administered about 1 hour to 1 week apart, such as 1, 2, 3, 4, 5, 6, 7, 8, 9, 10, 11, 12, 13, 14, 15, 16, 17, 18, 19, 20, 21, 22, 23, or 24 hours apart, or 2, 3, 4, 5, 6, or 7 days apart. According to some embodiments, each dosage of the PEGylated medicine is administered about 4 hours apart, such as 4, 5, 6, 7, 8, 9, 10, 11, 12, 13, 14, 15, 16, 17, 18, 19, 20, 21, 22, 23, or 24 hours apart, or 2, 3, 4, 5, 6, or 7 days apart. According to other embodiments, more preferably, each dosage of the PEGylated medicine is administered about 8 hours apart, such as 8, 9, 10, 11 12, 13, 14, 15, 16, 17, 18, 19, 20, 21, 22, 23, or 24 hours apart, or 2, 3, 4, 5, 6, or 7 days apart. According to further embodiments, each dosage of the PEGylated medicine is administered about 7 days apart, such as 7, 8, 9, 10, 11 or 12 days apart.

The mixture of the anti-PEG antibody and hydrogel is prepared by mixing the anti-PEG antibody and the hydrogel in a ratio from about 1:1 to 1:100 (v/v), such as from about 1:1 to 1:50 (v/v), or from 1:1 to 1:20 (v/v). Preferably, the anti-PEG antibody and the hydrogel are mixed in a ratio of about 1:3 (v/v) to about 1:5 (v/v), such as about 1:3 (v/v), about 1:4 (v/v), or about 1:5 (v/v). More preferably, the anti-PEG antibody and the hydrogel is mixed in a ratio of about 1:4 (v/v). In general, the mixture of the anti-PEG antibody and the hydrogel is used as an adjuvant to a PEGylated medicine, meaning the mixture by itself does not produce any therapeutic effects with respect to the treatment of the disease, rather it is to help retaining and/or routing the PEGylated medicine to its target site within the subject.

Accordingly, the mixture may be used with any PEGylated medicine, which includes, but is not limited to, Pegasys (a PEGylated interferon alpha 2A for the treatment of chronic hepatitis C or B), Peginsatide (a PEGylated medicine for treating anemia associated with chronic kidney disease in adult patients on dialysis), Pegloticase (a PEGylated uricase for treating gout), Certolizumab pegol (a PEGylated monoclonal antibody for treatment of moderate to severe rheumatoid arthritis, Crohn's disease, or an inflammatory gastrointestinal disorder), Methoxy PEG-epoetin beta (a PEGylated erythropoetin for treating anemia associated with chronic kidney disease), Pegaptanib (for treating neovascular age-related macular degeneration), Pegfilgrastim or Neulasta (a PEGylated recombinant methionyl human granulocyte colony-stimulating factor for treating sever cancer chemotherapy-induced neutropenia), Pegvisomate (a PEG-human growth hormone mutein antagonist for the treatment of acromegaly), Doxambicin liposome (a PEGylated liposome containing doxorubicin for the treatment of cancer), Pegaspargase (a PEGylated L-asparaginase for the treatment of acute lymphoblastic leukemia), Pegademase bovine (a PEGylated adenosine deaminase for the treatment of severe combined immunodeficiency disease (DSID)); and PEGylated anti-ischemia agent such as PEGylated Mechano growth factor (PEG-MGF) and PEGylated granulocyte colony-stimulating factor (PEG-G-CSF). In one preferred embodiment, the PEGylated medicine is PEGylated doxorubicin liposome. In another preferred embodiment, the PEGylated medicine is a combination of PEG-MGF and PEG-G-CSF.

According to embodiments of the present disclosure, the PEGylated medicine administered to the subject at each applications is the same or different therapeutics. Further, the PEGylated medicine and the mixture of the anti-PEG antibody and hydrogel are respectively administered to different sites via different routes. In one example, the mixture of the anti-PEG antibody and hydrogel is administered directly by intramuscular injection to the ischemia area (e.g., the myocardial infarction site), whereas the PEGylated medicine is administered intravenously from a site on the limb (i.e., arm or leg).

Specifically, the present disclosure provides a method of treating a subject suffering from an ischemia disease. The method comprises administering to the subject, a sufficient amount of the mixture of the present invention, and an effective amount of a PEGylated medicament (e.g., a PEGylated anti-ischemia agent) for treating the ischemia disease given in at least two independent dosages, with each dosage being given at least 8 to 24 hours apart; so as to ameliorate one or more symptoms related to ischemia disease.

The subject may be a mammal, preferably a human; and the ischemia disease may be stroke, myocardial infarction (MI) or limb ischemia. In one embodiment, the ischemia disease to be treated is MI. In another embodiment, the ischemia disease to be treated is limb ischemia, which may be any of critical limb ischemia, acute limb ischemia or Buerger's Disease.

In some embodiments, the PEGylated anti-ischemia agent is administered in two independent applications. In other embodiments, the PEGylated anti-ischemia agent is administered in three independent applications.

The present disclosure also encompasses a method of treating a subject suffering from a cancer. The method comprises administering to the subject, a sufficient amount of the mixture of the present invention, and an effective amount of a PEGylated anti-cancer drug given in at least two independent dosages, with each dosage being given at least 1 week apart; so as to ameliorate one or more symptoms related to cancer.

The subject may be a mammal, preferably a human; and the cancer may be any of breast cancer, cervical cancer, ovary cancer, endometrial cancer, melanoma, uveal melanoma, brain tumor, lung cancer, liver cancer, lymphoma, neuroepithelioma, kidney cancer, bladder cancer, pancreatic cancer, prostate cancer, stomach cancer, colon cancer, uterus cancer, hematopoietic tumors of lymphoid lineage, myeloid leukemia, thyroid cancer, thyroid follicular cancer, myelodysplastic syndrome (MDS), tumor of mesenchymal origin, teratcarcinoma, neuroblastoma, glioma, glioblastoma, keratoacanthomas, analplastic large cell lymphoma, esophageal squamous cell carcinoma, follicular dentritic cell carcinoma, intestinal cancer, muscle invasive cancer, seminal vesicle tumor, epidermal carcinoma, spleen cancer, head and neck cancer, stomach cancer, bone cancer, cancer of retina, biliary cancer, small bowel cancer, salivary gland cancer, uterine sarcoma, cancer of testicles, cancer of connective tissue, prostatic hypertrophy, myelodysplasia, Waldenstrom's macroglobulinemia, nasopharyngeal, neuroendocrine cancer, mesothelioma, angiosarcoma, Kaposi's sarcoma, oesophagogastric, fallopian tube cancer, peritoneal cancer, papillary serous mullerian cancer, malignant ascites, gastrointestinal stromal tumor (GIST), Li-Fraumeni syndrome or Von Hippel-Lindau syndrome (VHL).

The hematopoietic tumors of lymphoid lineage may be any of leukemia, acute lymphocytic leukemia, chronic lymphocytic leukemia, B-cell lymphoma, Burkitt's lymphoma, multiple myeloma, Hodgkin's lymphoma, or Non-Hodgkin's lymphoma. The myeloid leukemia may be acute myelogenous leukemia (AML) or chronic myelogenous leukemia (CML). The tumor of mesenchymal origin is fibrosarcomas or rhabdomyosarcomas.

In some embodiments, the PEGylated anti-cancer drug is administered in two independent dosages. In other embodiments, the PEGylated anti-cancer drug is administered in three independent dosages.

The mixture of this invention (i.e., the mixture of the anti-PEG antibody and the hydrogel), as well as the PEGylated therapeutic, may be administered to a mammal, preferably human, by any route that may effectively transports the mixture and/or the PEGylated therapeutic to the appropriate or desired site of action, such as oral, nasal, pulmonary, transdermal, such as passive or iontophoretic delivery, or parenteral, e.g., rectal, depot, subcutaneous, intravenous, intramuscular, intranasal, intra-cerebella, ophthalmic solution or an ointment. Further, the administration of the mixture of this invention with the PEGylated therapeutic may be to the same or different sites of the subject, and may be concurrent or sequential.

Preferably, the mixture of the present invention may be formulated into liquid pharmaceutical compositions, which are sterile solutions, or suspensions that can be administered by, for example, intravenous, intramuscular, subcutaneous, or intraperitoneal injection; whereas the PEGylated medicine may be in any dosage form, which includes without limiting, solid or liquid dosage for oral, parenteral, nasal or sublingual administration. Suitable diluents or solvent for manufacturing sterile injectable solution or suspension of the mixture of the present invention include, but are not limited to, 1,3-butanediol, mannitol, water, Ringer's solution, and isotonic sodium chloride solution. Fatty acids, such as oleic acid and its glyceride derivatives are also useful for preparing injectables, as are natural pharmaceutically-acceptable oils, such as olive oil or castor oil. These oil solutions or suspensions may also contain alcohol diluent or carboxymethyl cellulose or similar dispersing agents. Other commonly used surfactants such as Tweens or Spans or other similar emulsifying agents or bioavailability enhancers that are commonly used in manufacturing pharmaceutically acceptable dosage forms can also be used for the purpose of formulation. Oral administration may be either liquid or solid composition form.

It will be appreciated that the dosage of the mixture of the present invention will vary from patient to patient not only for the particular anti-PEG antibody or PEGylated therapeutic selected, the route of administration, and the ability of the PEGylated therapeutic to elicit a desired response in the patient, but also factors such as disease state or severity of the condition to be alleviated, age, sex, weight of the patient, the state of being of the patient, and the severity of the pathological condition being treated, concurrent medication or special diets then being followed by the patient, and other factors which those skilled in the art will recognize, with the appropriate dosage ultimately being at the discretion of the attendant physician. Dosage regimens may be adjusted to provide the desired response. Preferably, the mixture of the present invention are administered at an amount and for a time such that at least one dosages of the PEGylated therapeutic (e.g., 2, 3, 4 or even more dosages, as long as the anti-PEG antibody is present to direct the PEGylated therapeutic to the treatment site) may be administered subsequently to the subject to achieve an improved therapeutic response.

The present invention will now be described more specifically with reference to the following embodiments, which are provided for the purpose of demonstration rather than limitation.

EXAMPLES

Materials and Methods

Preparation of Fluorescent-Conjugated AGP4 and HA Hydrogel

AGP4 (IgM mAb against PEG) was generated by immunizing female BALB/c mice with PEG-derived proteins in accordance with the procedures described previously (Su, Y. C. et al., Bioconjugate Chemistry (2010) 21, 1264-1270). HA powder (1,500 kDa; Creative PEGworks, Winston-Salem, N.C., USA) was dissolved in phosphate-buffered saline (PBS), which was filtered through 0.22 µm filter at 4° C. to form a 2% (w/v) HA hydrogel. Alexa Fluor 647-(Invitrogen, Carlsbad, Calif., USA) conjugated AGP4 was prepared in according to the manufacturer's instructions, and the conjugating ratio was 40:1 (w/w). The Alexa Fluor 647-conjugated AGP4 and HA (the ratio was 1:4 (v/v)) were then mixed and gently agitated at 4° C. to form the final product, 2% (w/v) HA-AGP4 hydrogel.

Sandwich ELISA

The sandwich ELISA was conducted in according to previously described procedures (Su, Y. C. et al., Bioconjugate Chemistry (2010) 21, 1264-1270). Briefly, 5 µl/mL AGP4- and normal mouse IgM-coated (Jason Lab, USA) plates were prepared, then the graded concentrations of PEG-Qdot 800 and Lipo-Dox (50 µl/well) in dilution buffer were added to the coated wells for 2 h at room temperature. After washing with PBS-T (PBS containing 0.1% Tween-20) three times and PBS twice, the plates were sequentially covered with 50 µL/well detection antibody (5 µg/mL 3.3-biotin) for 1 h and then 0.5 µg/mL HRP-conjugated streptavidin for 1 h at room temperature. The plates were washed with PBS-T six times and with PBS two times and 100 µL/well ABTS substrate (0.4 mg/mL 2,2'-azino-di(3-ethyl-benzthiazoline-6-sulfonic acid), 0.003% $H_2O_2$, 100 mM phosphate citrate, pH 4.0) was added for 30 min at room temperature. The absorbance of the wells at 405 nm was measured by microplate reader.

Experimental Animals

All procedures involving animal research were approved by the Experimental Animal Committee, Academia Sinica. An adult female FVB mice model (6~8-week-old, 25 g) were obtained from the National Laboratory Animal Center. Briefly, all mice were anesthetized with Zoletil (12.5 mg/kg; Virbac, Carros, 162 France) and Rompun (0.2 ml/kg; Bayer Healthcare, Kiel, Germany) before surgery and in vivo measurements.

Navigated Testaments and Quantification

2% HA-AGP4 hydrogel of the present disclosure were injected subcutaneously to 3 different locations of the front side (50 µl for each site) or intramuscularly of the right leg in mice (50 µl for each site, total volume: 200 µl), the PEG-Qdot 800 was given immediately via intravenous injection. Moreover, the triple administrations of PEG-Qd800 were employed to demonstrate the reloadable functionality achieved by 2% HA-AGP4 hydrogel of the present disclosure. The mice were imaged using a Xenogen IVIS Spectrum device (PerkinElmer, Waltham, Mass., USA) and the corresponding filter sets. The fluorescent intensity was determined by calculating the number of photons within the manually drawn regions of interest (ROI), and the intensity was adjusted to exclude tissue autofluorescence of the control group.

Animal Model of Hindlimb Ischemia (HLI) and Treatment

The HLI model was created by performing the left femoral artery and iliac artery ligation in mice and then cut to induce hindlimb ischemia (Limbourg et al., Nat. Protocols (2009) 4, 1737-1748.). The administrations for the experimental mice were divided into 3 parts: PEG-IGF-1, PEG-G-CSF, and the combined treatment. The treatment of PEG-IGF-1 and PEG-G-CSF are including five groups: Sham, HLI with the treatment of, 2% HA alone plus therapeutics or HA with AGP4 and followed by PBS or therapeutics. The combined treatment are including three groups: Sham, HA/AGP4 followed by combined therapeutics or PBS. The 2% hydrogel were injected intramuscularly, which injections were delivered into 4 sites at the ischemic area (50 µl for each site, total volume: 200 µl) and PBS or therapeutics were delivered sequentially by intravenous injection.

Blood Flow Measurement

Microvascular blood flow was measured on a laser Doppler imager (Moor Instrument, UK). The blood flow before surgery, 1 day afterwards, every week for the following 4 weeks was recorded for both limbs and before sacrificing the mice. The data are presented as the blood flow ratio of the ischemia limb (left) to the normal limb (right).

Immunofluorescence Staining

The fixed distal calf and thigh muscles were deparaffinized, rehydrated and boiled in 10 mM sodium citrate (pH 6.0) for 10 minutes, followed by incubation with antibodies against tropomyosin (DHSB, Iowa city, Iowa, USA), WGA and isolectin (Invitrogen, Grand Island, N.Y., USA) at 4° C. overnight, and then incubated with Alexa Fluor 488- or 568-conjugated secondary antibodies (Invitrogen, Carlsbad, Calif., USA). After staining with DAPI (Sigma-Aldrich, St. Louis, Mo., USA), sections were mounted and observed under confocal microscope (LSM 700, Carl Zeiss MicroImaging, Germany) and fluorescence microscope. The capillary and arteriole densities at the border zone were measured and images were taken from 8 randomly-selected ischemic areas (200× magnification) in each sample and quantification was performed by manually counting each section; the 8 values were averaged.

Clinical Scoring of Mice After Hind-Limb Ischemia (HLI)

The clinical score of the mice after receiving the different treatments were obtained in accordance with procedures described previously (Lai, C. Y. et al., Biomacromolecules (2013) 15, 564-573.). Clinical scores were estimated based on daily observation of mouse activity and hindlimb condition; and the scores were categorized into 7 stages from 0 (normal), 1~3 (muscle atrophy), 4~5 (occurrence of gangrene) to 6 (limb amputation).

Statistical Analysis

All data are presented as mean±standard deviation unless otherwise indicated (n=3 for in vitro spectrum analysis, n=6 for in vivo navigated testaments, n=8 for hindlimb ischemic model and treatments). For multiple comparisons, analysis of variance (ANOVA) with Bonferroni adjustment was performed. A probability value of $P<0.05$ was considered to represent statistical significance.

Example 1 Establishing Animal Model for Multiple Administration of PEGylated Compound with the Aid of Anti-PEG Antibody and HA

1.1 The Anti-PEG Antibody Binds Specifically to PEGylated Compounds

In this example, the binding profile (FIG. 1A) and efficiency (FIG. 1B) of a PEGylated compound (i.e., PEGylated QDot (PEG-Qd800)) to anti-PEG antibody (i.e., AGP4) were respectively determined by sandwich ELISA assay.

Figure 1B:
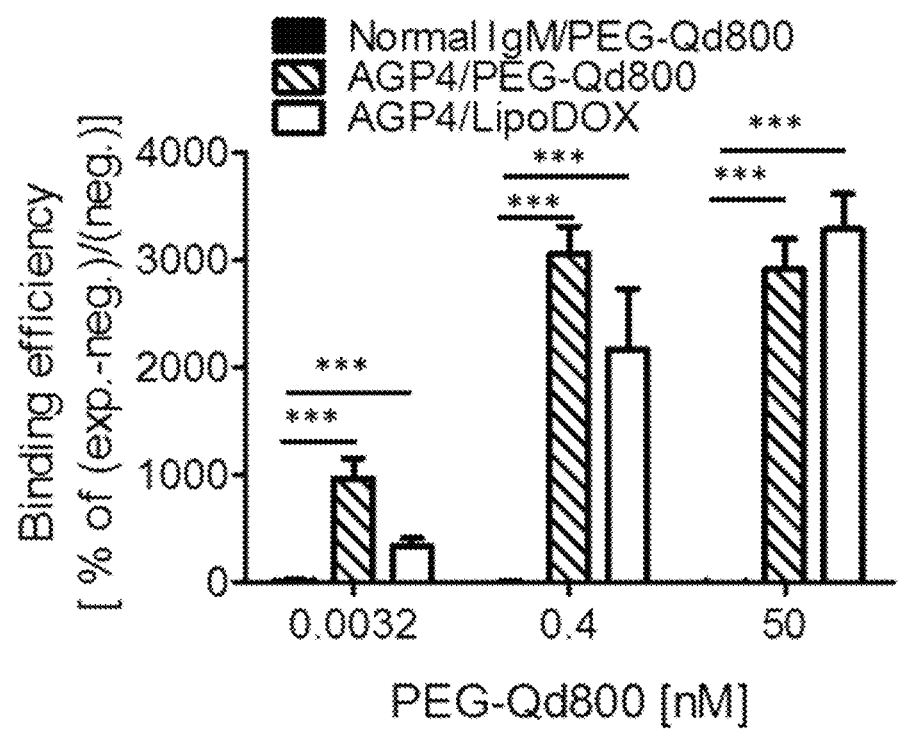

As depicted in FIG. 1A, PEG-Qd800 did not react with none-coated wells (●) or normal IgM-coated wells (■). In contrast, a dose-dependent absorbance reading was seen with AGP4-coated wells. As the amount of PEG-Qd800 increased, so did the absorbance readings of the AGP4-PEG-Qd800 complexes (▲). The same effect was also seen with commercially available PEGylated liposomal doxorubicin (PEG-Lipo), although the reading began to saturate after the concentration reached 10 nM (▼). Compared to IgM, it was found that the AGP4 antibody would bind to either PEG-Qd800 or Lipo-DOX with similar binding efficiency (FIG. 1B).

Further, the fluorescence signals respectively produced from AGP4 (encapsulated in HA hydrogel) and PEGylated compounds, were demonstrated to be independent of each other, both in vitro and in vivo, in which the excitation wavelengths of Alexa 647 dye-labeled AGP4 and PEG-Qd800 were respectively set at 605 nm and 465 nm.

1.2 In Vivo Targeting Profiles of PEG-Qd800

Figure 2A:
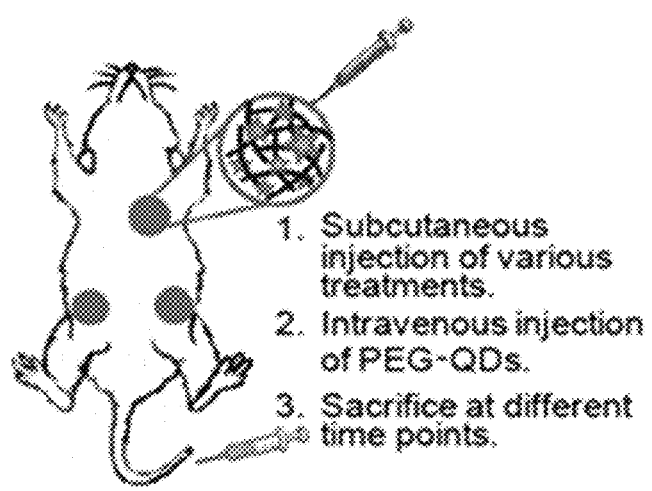
FIGS. 2A-2F: Targeting profile of PEG-Qd800 in in vivo mouse models.

In this example, the in vivo targeting profile of a PEGylated compound (e.g., PEG-QDs) was examined, in which a single dose of HA/AGP4 was subcutaneously injected to three different locations across the body of a single mouse, then a dose of PEG-Qd800 was administered 10 minutes afterwards via intravenous injection through the tail vein (see FIG. 2A).

Figure 2B:
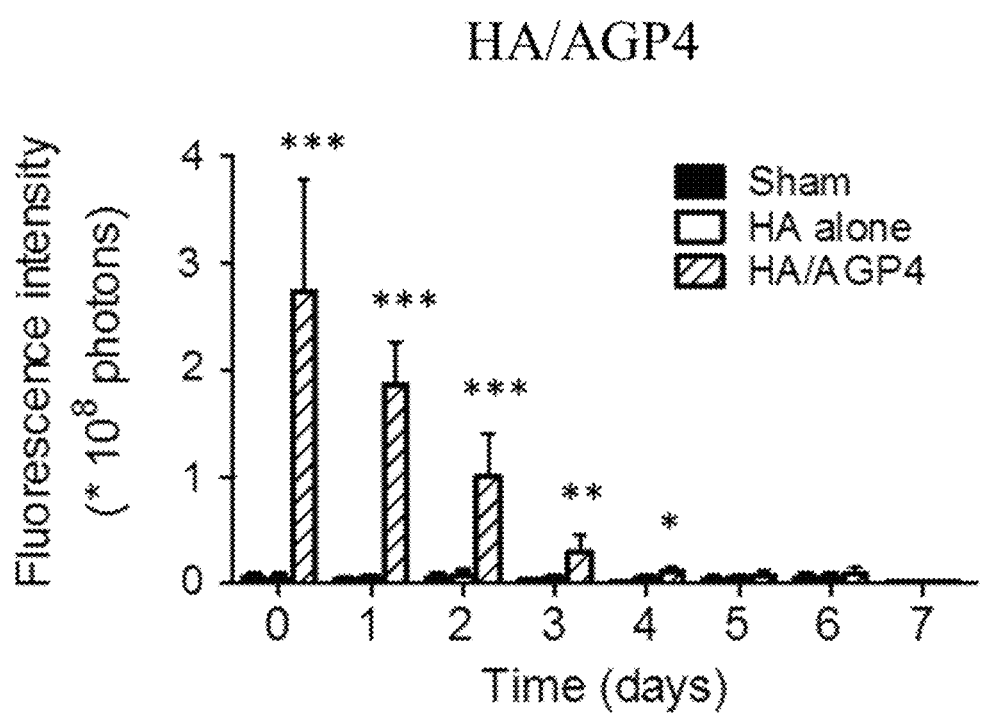
Figure 2C:
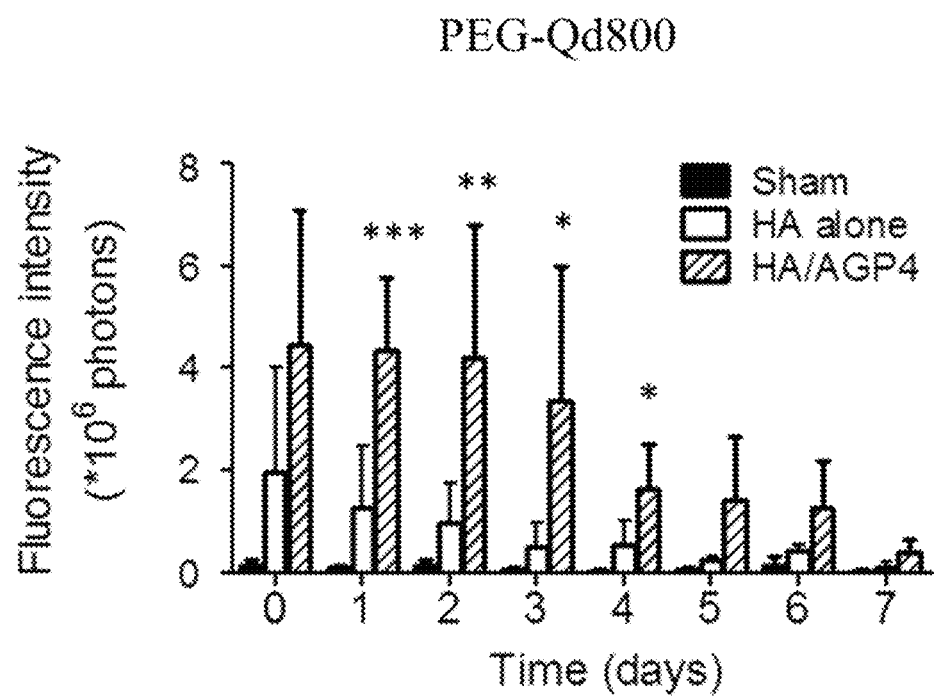

Compared with the sham and HA-alone groups, the fluorescence signal of AGP4 was visible from Day 1 till Day 3, while the fluorescent signal of HA-alone group remained negligible. By contrast, for mice that were treated with PEG-Qd800, the signals for PEG-Qd800 were visible from day 1 until Day 6, although the signals gradually diminished along with the progression of time. Furthermore, unlike the HA-alone group, the presence of AGP4 enhanced the recruitment and retention of PEG-Qd800 at all three subcutaneous injection sites. Although, PEG-Qd800 was positively detected in the HA-alone group at one of the subcutaneous injection sites, yet the signal was not visible from Day 2 onwards. The detected fluorescent signals of either HA/AGP4 or PEG-Qd800 were further quantified and summarized in FIGS. 2B and 2C, respectively.

Figure 2D:
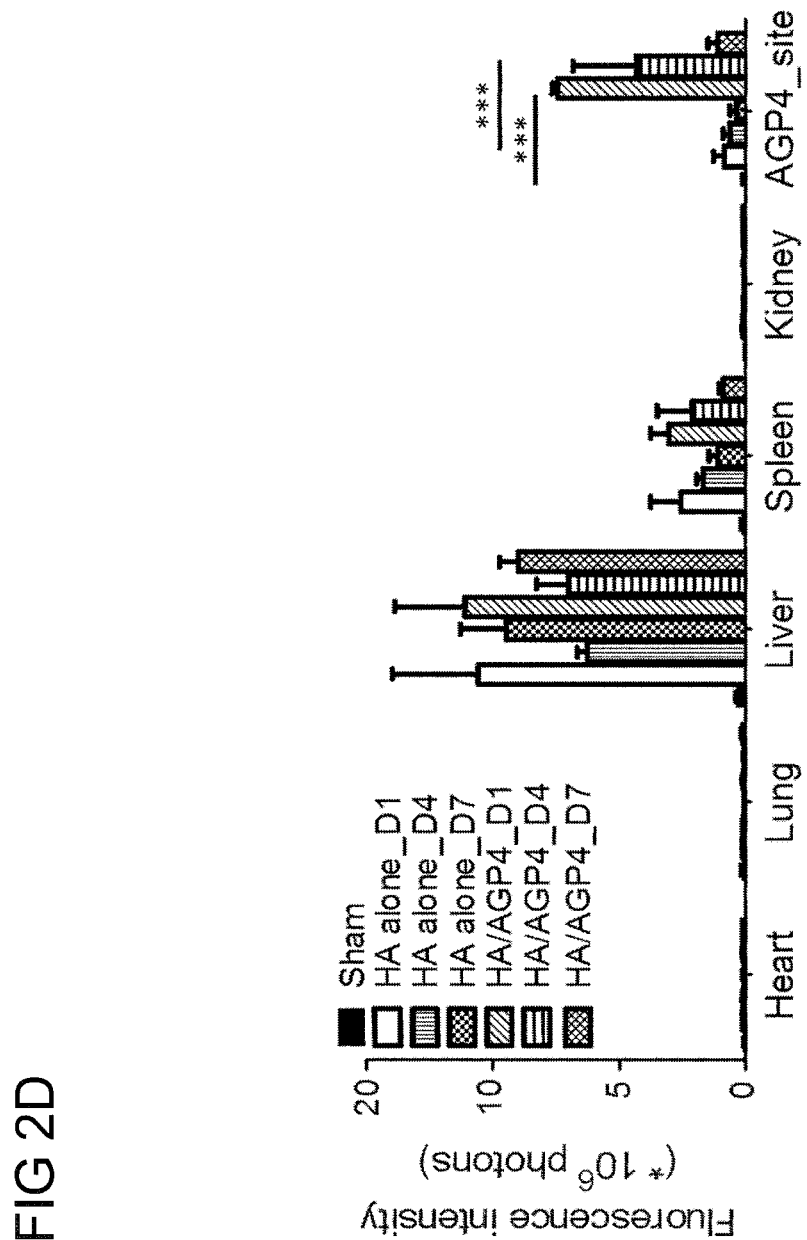
Figure 2E:
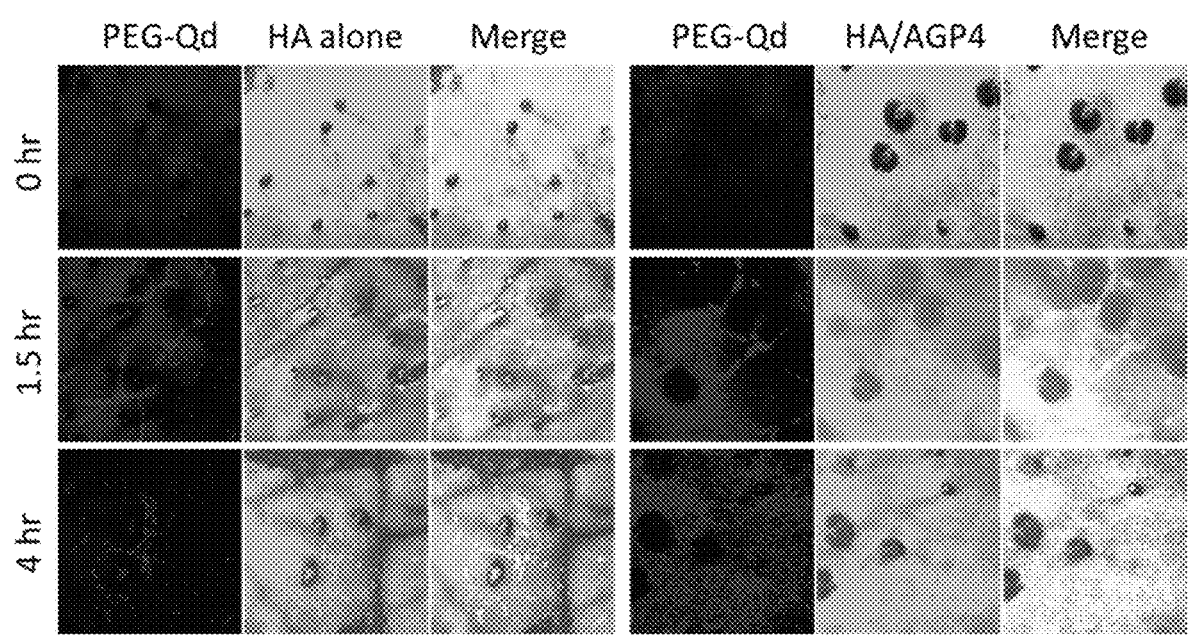
Figure 2F:
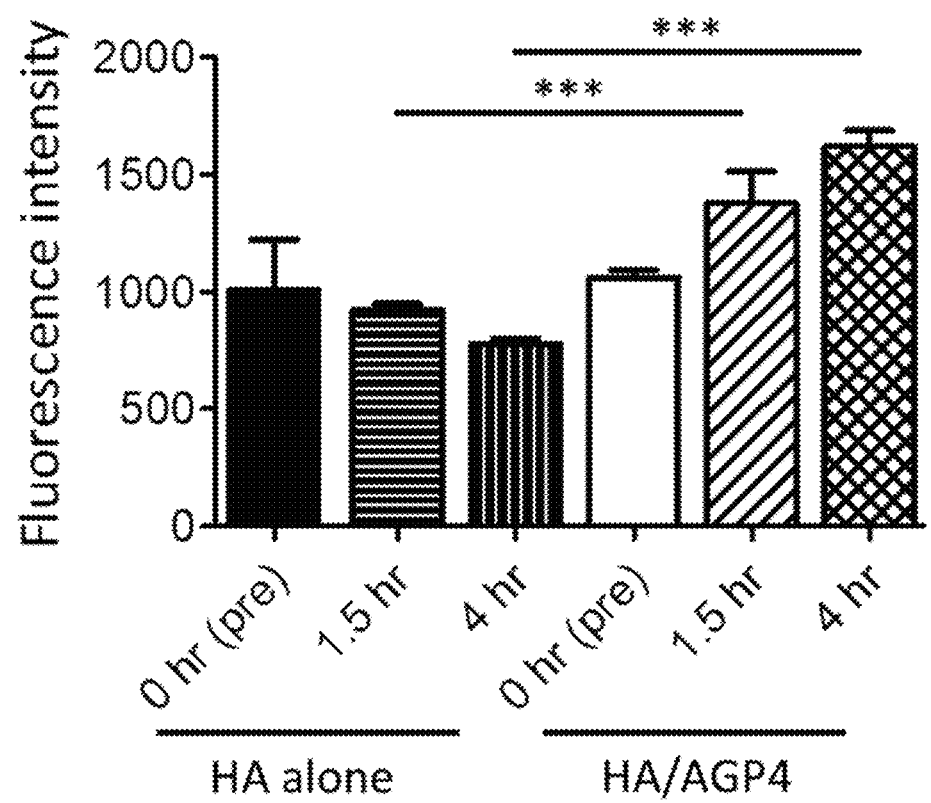

The fluorescence analysis of the organs isolated on the $1^{st}$, $4^{th}$ and $7^{th}$ day revealed that most of the PEG-Qd800 were retained in the liver at any of the three days compared with other organs (FIG. 2D). Not only had the differences between each day was minimal, nor was there any significant difference between the HA-alone and HA/AGP4 groups in any of the organs. However, significant differences were observed at the AGP4 injected sites (AGP4 site). Compared with the HA-alone group, the presence of HA/AGP4 at the injection sites resulted in significantly higher level of PEG-Qd800 signals being detected at both the $1^{st}$ and $4^{th}$ day. The targeting capacity was also confirmed by utilizing intravital microscopy, results depicted in FIG. 2E demonstrated that the fluorescence signals from mice treated with HA/AGP4 gel or HA gel alone, may be observed through the FITC channel, 1.5 hours after the administration of PEG-Qd655 by iv injection, the circulated PEG-Qds would penetrate through blood vessels' wall and retained at the surrounding in HA/AGP4 group. As a comparison, in HA alone group, the PEG-Qds were stuck within the blood vessels even after being treated with PEG-Qds for 1.5 to 4 hours, the results indicated that HA/AGP4 treatment would significantly enhance the fluorescence intensity of PEG-Qd655, as compared to that of the HA alone group (FIG. 2F).

1.3 Multiple Administration of PEGylated Compound with the Aid of Anti-PEG Antibody and HA In the example, multiple application of a PEGylated compound (e.g., PEG-Qd800) with the aid of anti-PEG antibody and HA was evaluated. Thus, the fluorescence signal of PEG-Qd800 was examined after multiple injections of PEG-Qd800 along with the anti-PEG antibody and HA. Specifically, on day 0, a single intramuscular injection of HA/AGP4 was made to the right leg of the mice, followed by the first IV injection of PEG-Qd800; then the $2^{nd}$ and $3^{rd}$ IV injections of PEG-Qd800 were made on the following two days, respectively. Results are illustrated in FIG. 3.

Figure 3A:
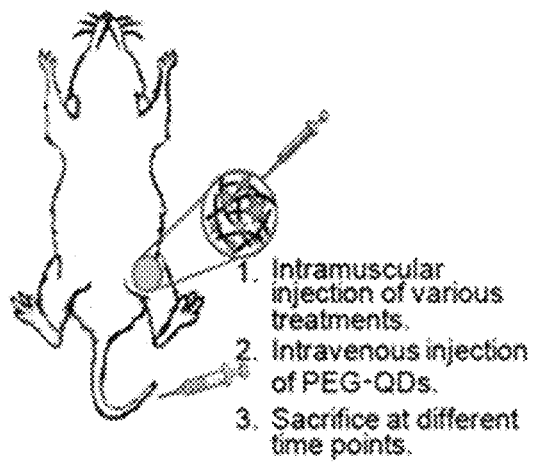
FIGS. 3A-3E: The fluorescence analysis of multiple administrations of PEG-Qd800.
Figure 3B:
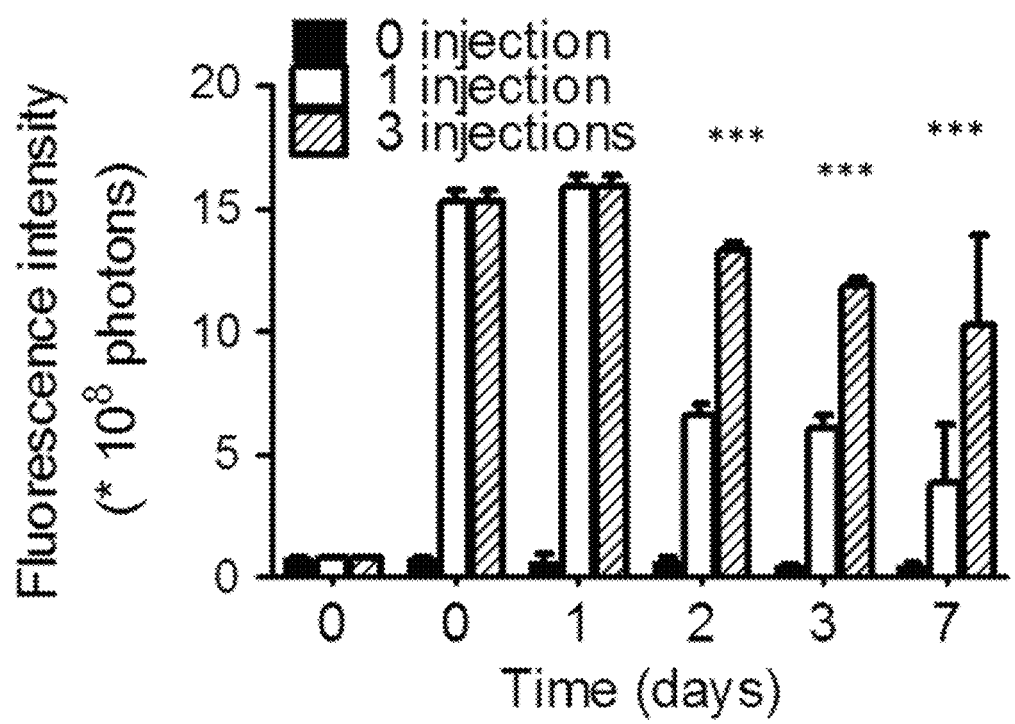

As depicted in FIG. 3A, after the intramuscular injection of HA/AGP4 to the right leg of the mice, the AGP4 signals in the right leg muscle tissues was still observable even on the $3^{rd}$ day, even though only one injection was made. Similarly, strong fluorescence signals of multiple injections of PEG-Qd800 were found on day 3, but not on day 7. Further, the mice designated to have a total three injections exhibited stronger signals of PEG-Qd800 compared to the other two groups, and the signals remained visible even on Day 7. By quantified the detected PEG-Qd800 signals, it was clear that the measured fluorescence intensity of the group of mice with three injections was significantly higher than the other two groups (FIG. 3B). Additionally, the differences of the measured signals between different days were insignificant for the mice with three injections. The result indicated that a significant number of PEG-Qd800 administered on different days were retained in the proximity of the HA/AGP4 injection site.

Figure 3C:
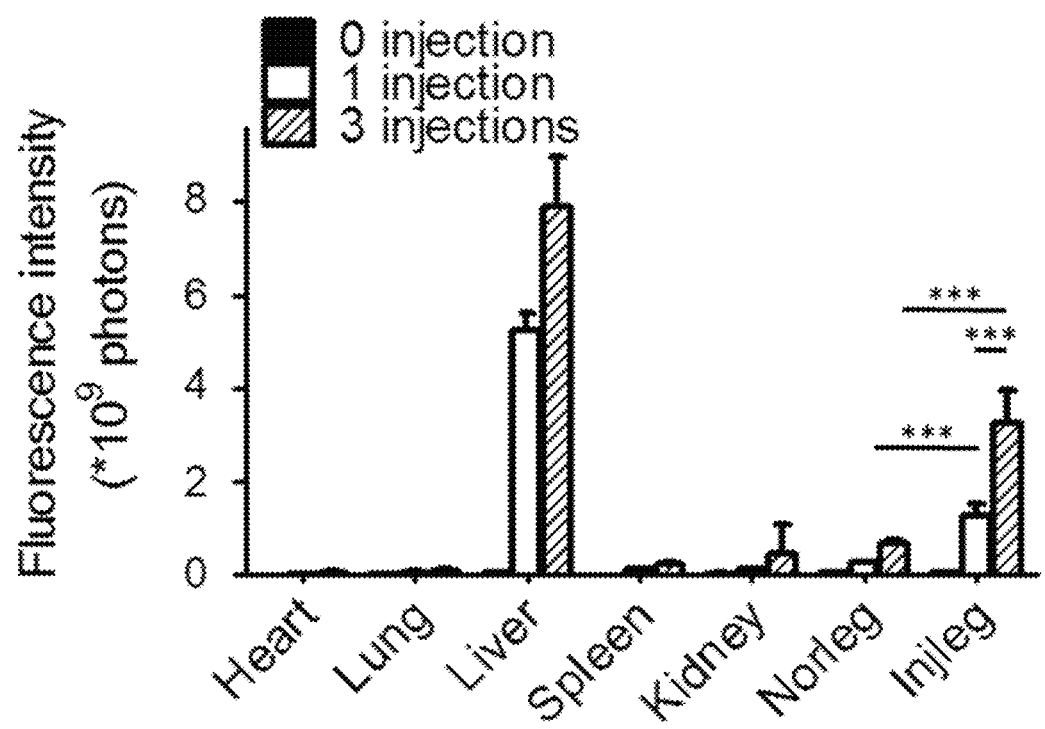
Figure 3D:
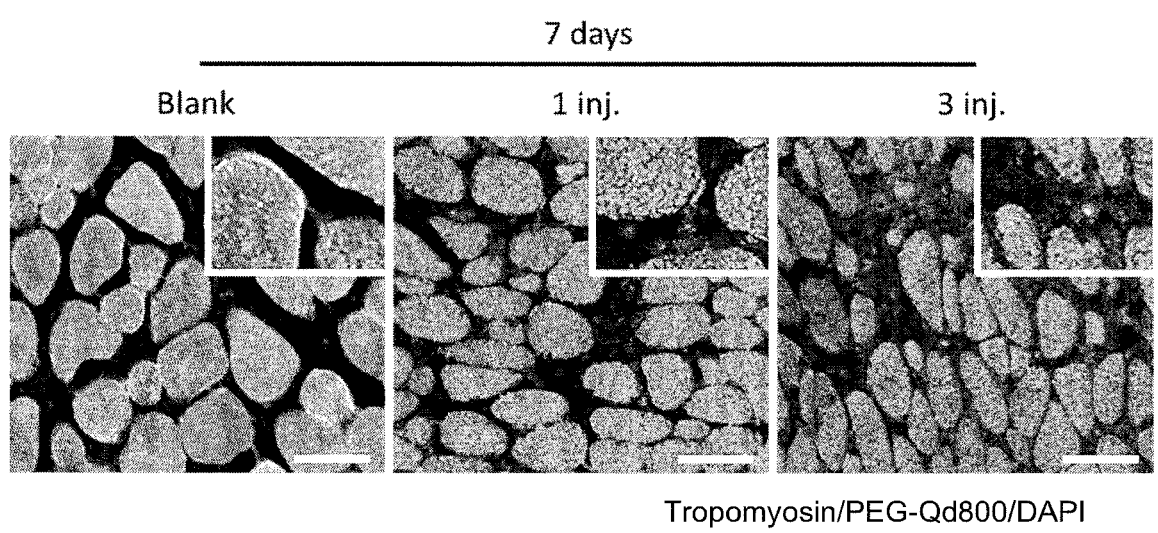

The biological significance of HA/AGP4 was further evidenced when evaluating the PEG-Qd800 signal in the leg muscles as well as in other organs, such as heart, liver, lung, spleen and kidney (FIG. 3C). Compared with the left leg muscle, the right leg muscle exhibited strong signals for the HA/AGP4, suggesting the HA/AGP4 injected at the right leg muscle remained at the injection site till at least $7^{th}$ day post-injection. The retention of PEG-Qd800 at the right leg was evidenced by the strong fluorescence signals at the injection site, although some PEG-Qd800 were detected at the left leg muscle due to circulation. Apart from the liver and spleen, the measured PEG-Qd800 signals seem to be insignificant when compared with the right leg muscles. Such result was also seen in the quantitative analysis of the organs removed from the mice with either one or three injections with PEG-Qd800 (FIG. 3D). Although strong signals were seen on Day 7 in the liver from mice with either one or three injections of PEG-Qd800, the rest of organs exhibited minimal levels of the PEGylated compounds as compared with that of the injected right leg muscle. Thus, the result indicated the administration of HA/AGP4 help retain significant amount of intravenously injected PEG-Qd800 at the injected sites. Moreover, the significant levels of PEG-Qd800 in the right leg muscles detected between the $1^{st}$ and $3^{rd}$ injections, indicating the initial injected HA/AGP4 can continue to retain any subsequent injected PEG-Qd800 to the proximity of the injected site.

Figure 3E:
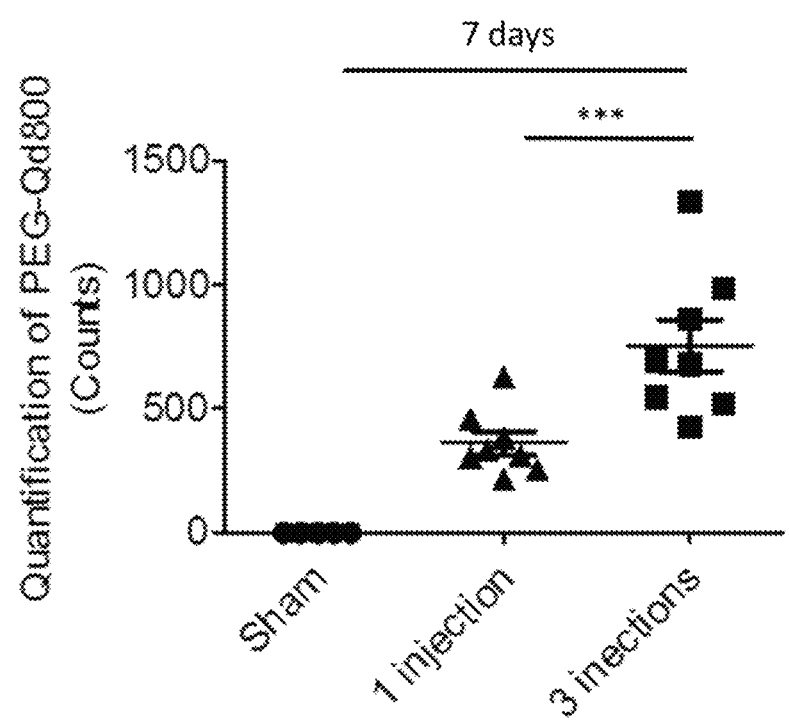

To quantitate the amounts of PEG-Qd800 at the tissue level on Day 7, immunohistochemistry (IHC) analysis was performed on the section of the right leg muscles that encompassed the HA/AGP4 injected site. Lower level of PEG-Qd800 staining was observed in mice with one injection as opposed to the mice that had three injections (FIG. 3D). Furthermore, no staining of PEG-Qd800 was observed in the left leg muscle (sham), which had not been treated with HA/AGP4. As depicted in FIG. 3E, the number of PEG-Qd800 at the injection site in each mice of each group was determined.

Taken together, the result confirmed the fact that subsequent intravenously injected PEG-Qd800 were indeed retained in the proximity of HA/AGP4 injected site, rather than being distributed into other organs.

Figure 4A:
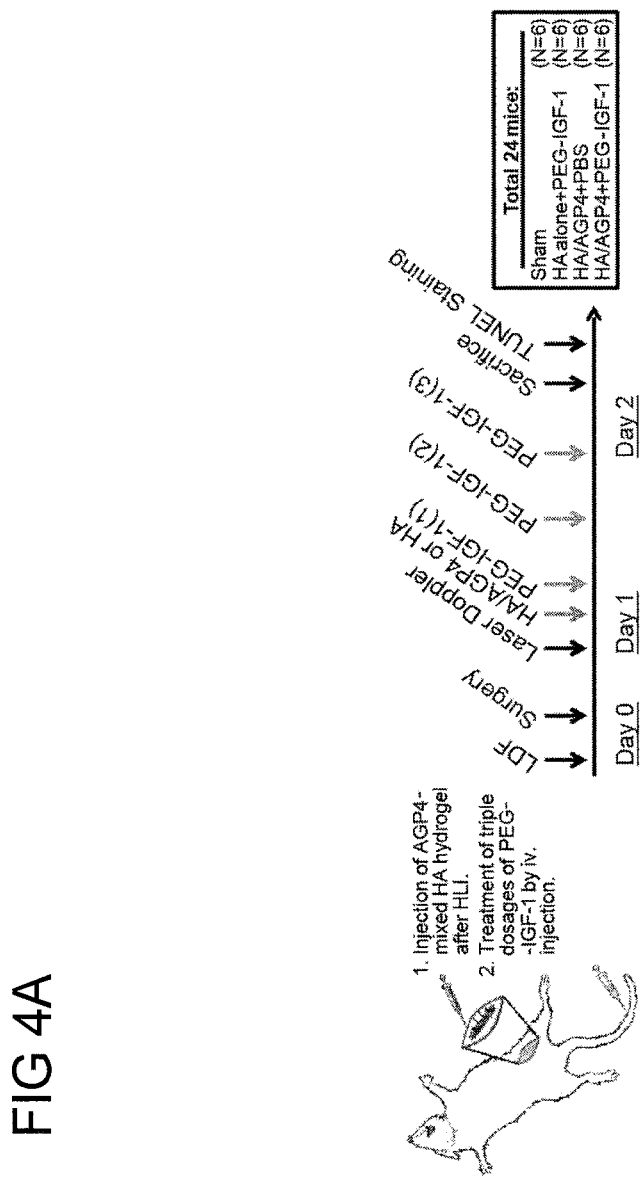
FIGS. 4A-4C: Analysis of therapeutic benefits of reloadable injections of PEGylated IGF-1 (PEG-IGF-1) in ischemic murine models.

Example 2 Multiple Injections of PEGylated Insulin Growth Factor-1 (PEG-IGF-1) Minimize Cell Death at HA/AGP4 Injection Site To verify whether multiple injection of PEGylated anti-ischemic compound administered at the HA/AGP4 injection site may improve ischemic injury such as by increasing blood flow to the ischemic area or by reducing the ischemic area, HLI animals of example 1 were treated with HA/AGP4, and PEGylated compound (e.g., PEG-IGF-1) or vehicle, and the effect of the PEGylated compound(s) on ischemic injury was monitored by detecting blood flow using Laser Doppler or by imaging the ischemic area. FIG. 4A is a schematic drawing illustrating the protocols and treatment regimen of this example. Specifically, HA and anti-PEG antibody were administered on day 1 after hind limb ischemia injury was created, and the first dose of PEG-IGF-1 (30 µg) was given to the test animals 10 minutes after the dose of HA/AGP4, the second dose of PEG-IGF-1 was also given on day 1 post HLI, followed by a dose of PEG-IGF-1 on day 2 post HLI. Note that each dose of PEG-IGF-1 was given sequentially at an interval of 8 hrs. Blood flow in ischemic area was continued monitored and the animals were eventually sacrificed and the muscle of the injured leg was stained for an estimation of the apoptosis level in the ischemic area. Results are depicted in FIGS. 4B to 4C.

Compared with sham group, the blood flow images taken after the surgery revealed that no significant improvement were found when the ischemic leg was treated with HA-alone+PEG-IGF-1 or HA/AGP4+PBS, at Day 1 or Day 2. However, there were signs of nail discoloration in the HA-alone+PEG-IGF-1 and HA/AGP4+PBS treatment groups. In contrast, such phenomenon was not obvious in the combination treatment group, in which PEG-IGF-1 was administered after the treatment of HA/AGP4. Thus, although the HA/AGP4 treatment did not improve the blood flow at the ischemic leg after PEG-IGF-1 injections, it did however minimized the ischemic damage.

Figure 4B:
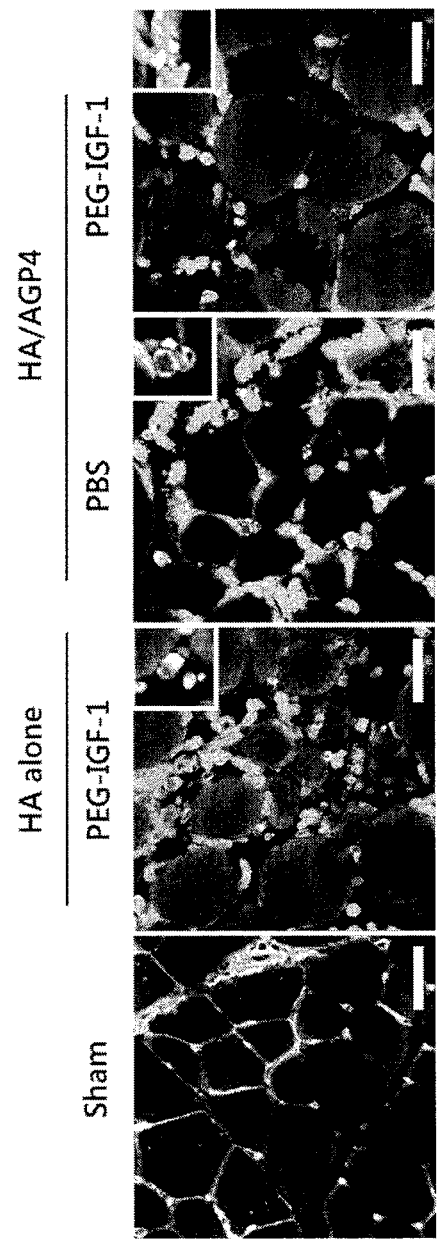
Figure 4C:
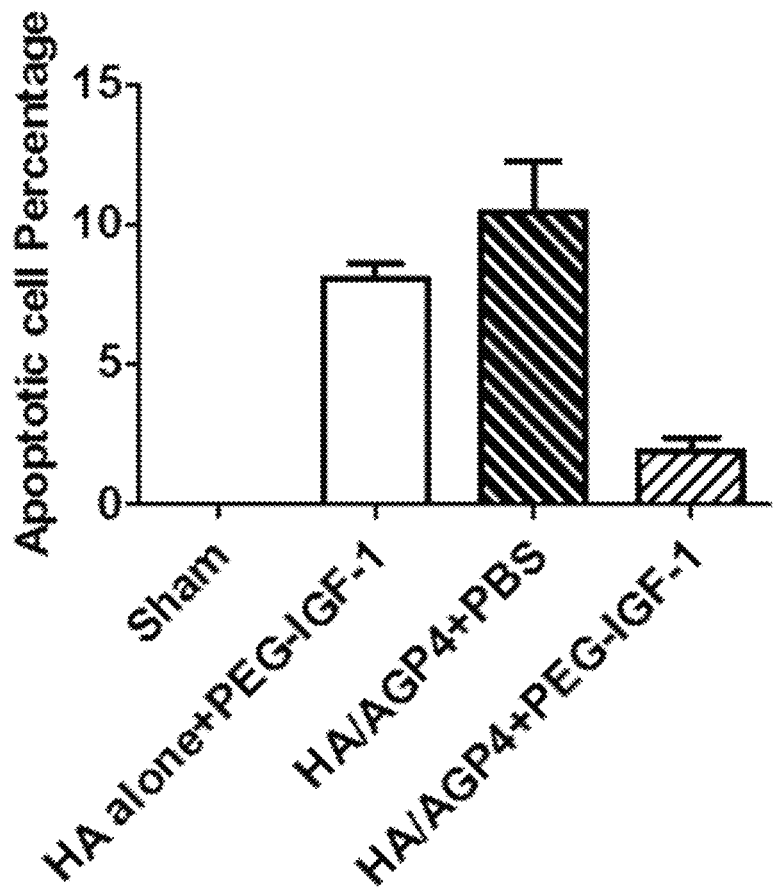

Since IGF-1 are known to enhance cell survival, the number of apoptotic cells presented at the HA/AGP4 injection site in the ischemic leg muscle was determined by TUNEL assay (FIGS. 4B and 4C). In the absence of AGP4, the administered PEG-IGF-1 failed to reduce the number of apoptotic cells in the HA-alone group. Similarly, the injection of PBS did not improve cell survival in the HA/AGP4 group. By contrast, the mice treated with PEG-IGF-1 after the administration of HA/AGP4 exhibited a significant reduction in apoptotic cells, suggesting the present HA/AGP4 system may help prolong the therapeutic effects of PEG-IGF-1.

Results of this example affirmed the use of HA in prolonging the life-time of anti-PEG antibody, which in term allowing multiple applications of PEGylated therapeutic to be administered to the subject in need of a treatment thereof.

Example 3 PEGylated Granulocyte Colony-Stimulating Factor (PEG-G-CSF) Retain at HA/AGP4 Injection Site Promotes the Cell Recruitments In this example, PEG-G-CSF was used as another PEGylated compound to evaluate its therapeutic effects at HA/AGP4 injection site using HLI model of example1, and the effect of the PEG-G-CSF on ischemic injury was monitored by detecting blood flow using Laser Doppler or by imaging the ischemic area.

Figure 5A:
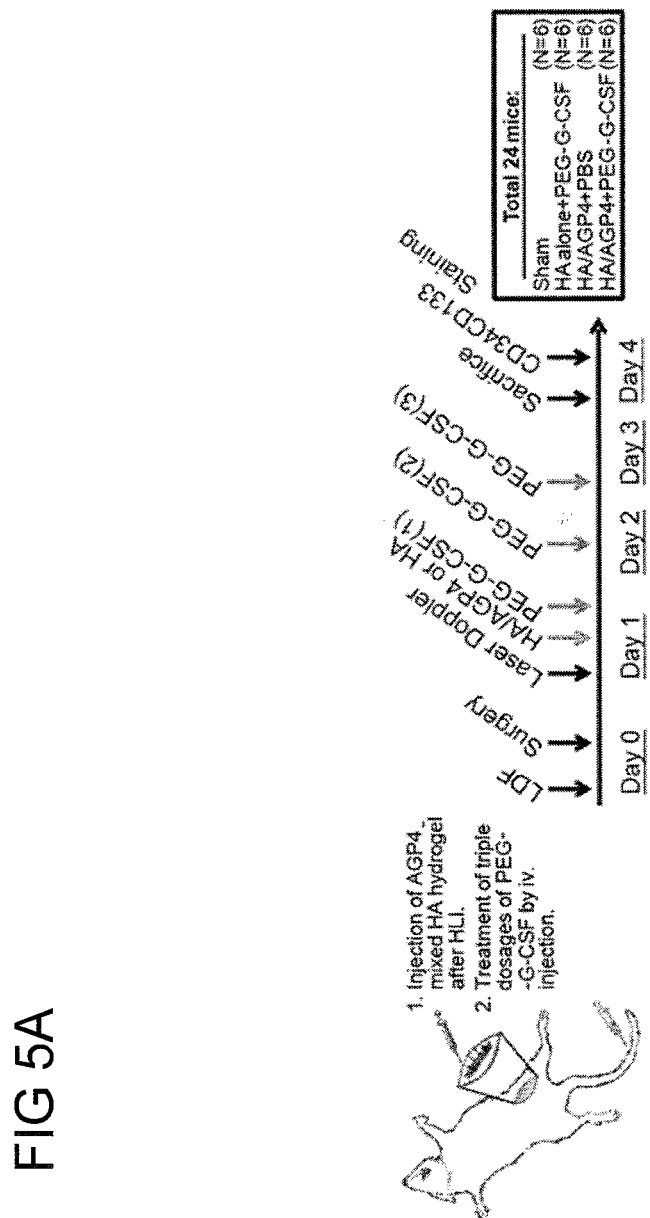
FIGS. 5A-5C: The analysis of therapeutic benefits of reloadable injections of PEGylated G-CSF (PEG-G-CSF) in ischemic mouse models.

FIG. 5A is a schematic drawing illustrating the protocols and treatment regimen of this example. Specifically, HA or HA/AGP4 (i.e., anti-PEG antibody) was administered on day 1 when hind limb ischemia injury was created, and the first dose of PEG-G-CSF was given to the test animals 10 minutes after the dose of HA or HA/AGP4, the second dose of PEG-G-CSF was given 24 hrs after the first dose of PEG-G-CSF on day 2, followed by a third dose of PEG-G-CSF on day 3 after the second dose of PEG-G-CSF. Blood flow in ischemic area was continued monitored and the animals were eventually sacrificed and the muscle of the injured leg was stained for an estimation of the density of recruited cells in the ischemic area. Results are depicted in FIGS. 5B to 5C.

Treatment with HA or HA/AGP4 alone failed to induce significant increase of blood flow in the ischemic area on Day 2 and 4 in mice; however, nail discoloration was seen in the HA-alone+PEG-G-CSF group and the HA/AGP4 group with PBS administration, but not in the HA/AGP4 group that had PEG-G-CSF injection.

Figure 5B:
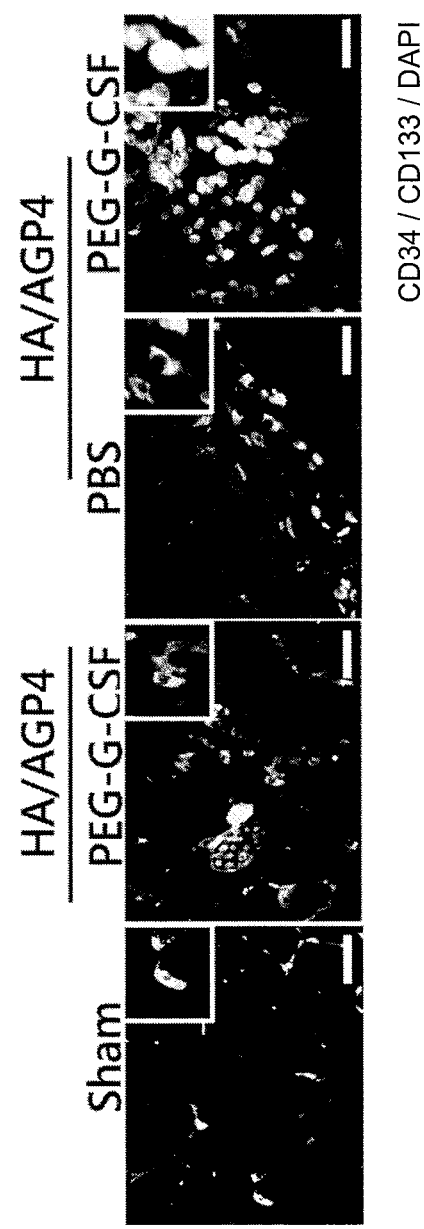
Figure 5C:
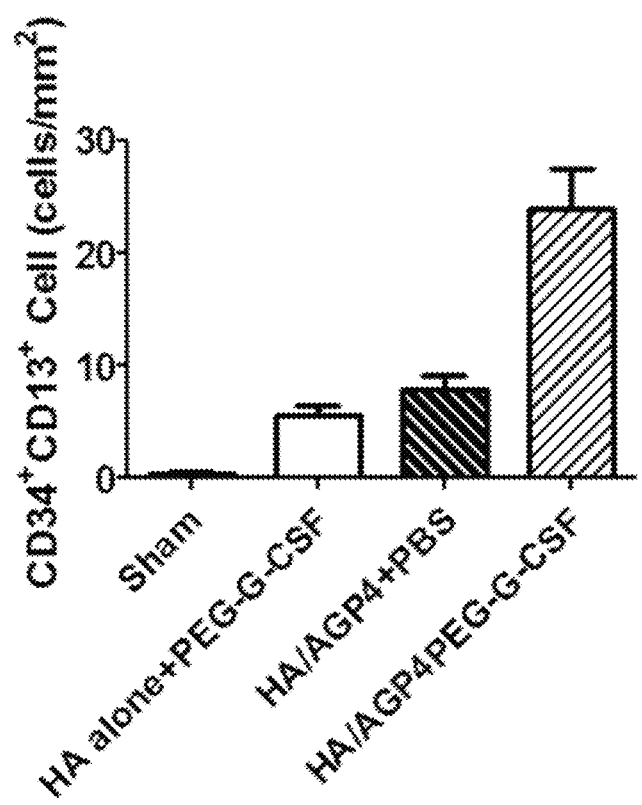

The ability of PEG-G-CSF in recruiting hematopoietic stem cells (HSCs) and endothelial progenitor cells (EPCs) at the HA/AGP4 injection site was also examined (FIGS. 5B and 5C). Compared with the HA-alone+PEG-G-CSF group and the HA/AGP4+PBS control, the injected PEG-G-CSF increased the number of HSCs (CD133) and ECs (CD34) presence at the HA/AGP4 injection sites (white arrows).

Example 4 Combined Delivery of the PEGylated Drugs Enhance Capillary Formation

Given that the therapeutic actions of PEG-IGF-1 and PEG-G-CSF are different to each other, it was decided to investigate the overall therapeutic effect of sequential delivery of both PEGylated therapeutics to the HA/AGP4 injection site in HLI mouse model.

Figure 6A:
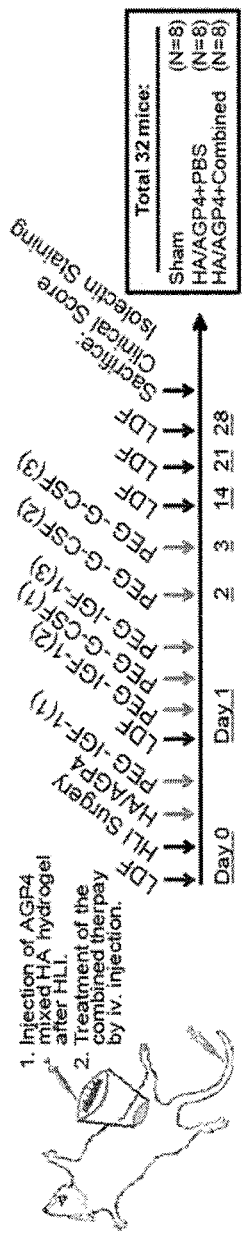
FIGS. 6A-6E. Improved therapeutic efficacy of combined therapy.
Figure 6B:
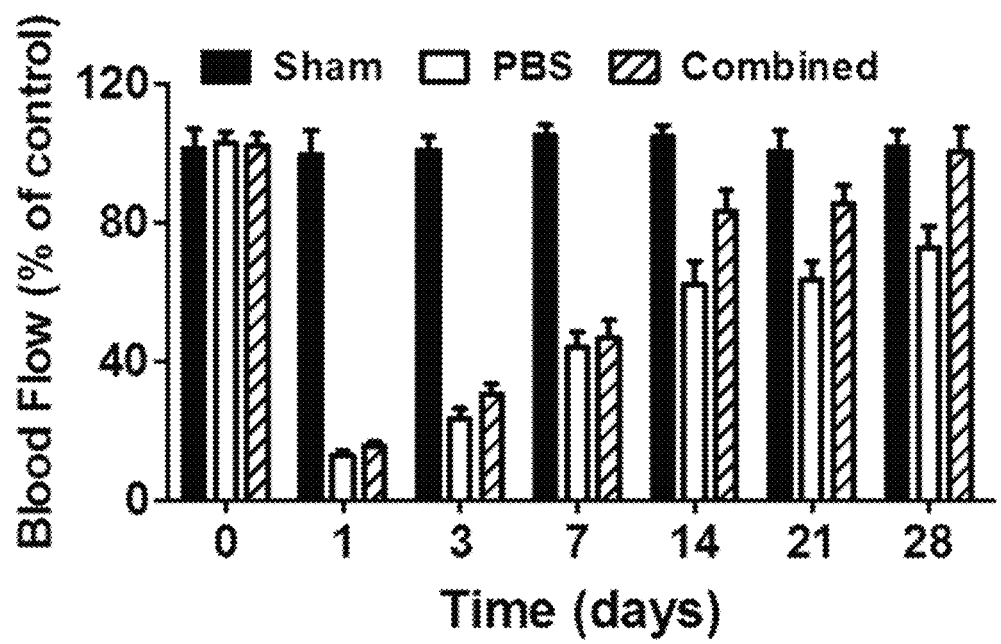
Figure 6C:
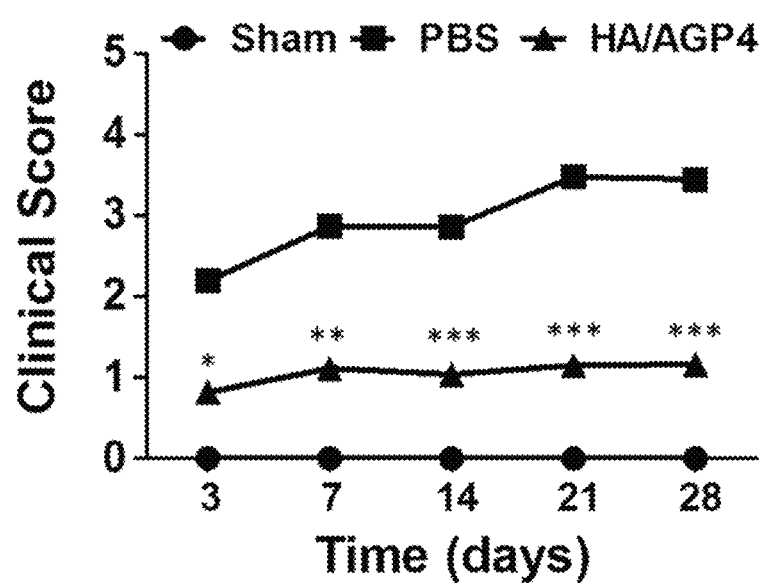

FIG. 6A is a schematic drawing illustrating the protocol of the present example, in which either PEG-IGF-1 or PEG-G-CSF was injected at various time points. Compared with the sham and the PBS control groups, the HA/AGP4 group that had the injections of both therapeutics displayed significant improvement in the blood flow as early as Day 14 (FIG. 6B). The significant differences in the blood flow continue to be seen between the PBS control and the group that had the combined delivery at Day 21 and Day 28. Moreover, the latter group displayed similar blood flow values as the sham group at Day 28. Although the PBS control group also displayed improvements in blood flow throughout the 28 days period, the mice exhibited signs of muscle atrophy as early as Day 7, and toe necrosis at Day 21 (FIG. 6C). In contrast, the physical appearance of the toes of the HA/AGP4 group with combined delivery was similar to the sham group.

Figure 6D:
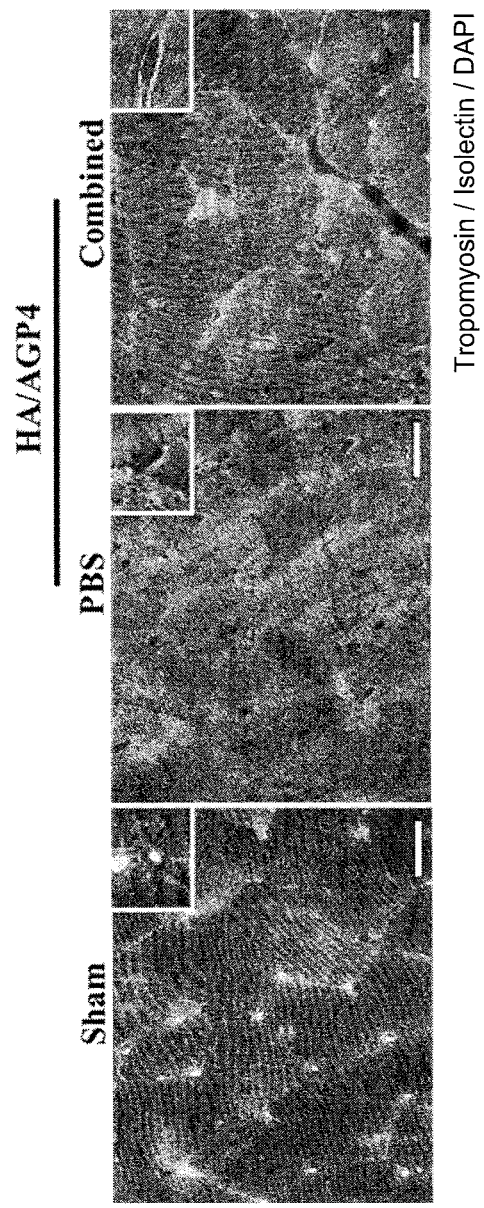
Figure 6E:
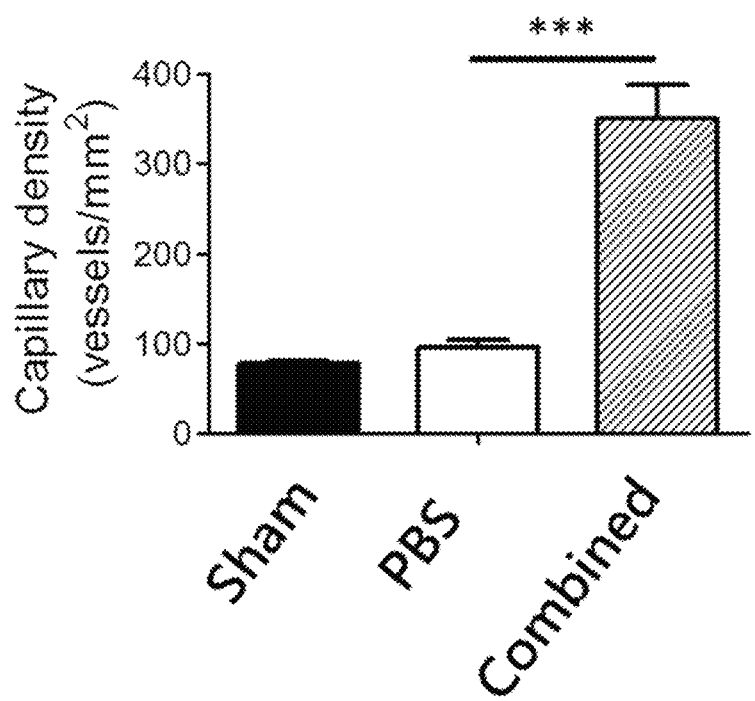

To further verify whether the combined delivery did improve the blood flow at the HA/AGP4 injection site, the tissue section that encompassed the site was stained for the presence of capillaries (FIGS. 6D and 6E). Similar to the sham group, the fluorescence staining of the tissue sections of the combined delivery group revealed large number of capillaries in the ischemic tissue (white arrows). In comparison, the PBS control group had relatively small number of capillaries in the stained tissues.

Results from the above examples confirm that administering HA and anti-PEG antibody at the same time to an intended target site in a subject help retaining the anti-PEG antibody at the treatment site for a longer period, which makes it possible to deliver multiple applications (e.g., 2 to 3 applications) of the PEGylated medicine afterwards to the subject, and thereby improves therapeutic effects.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A method of administering a PEGylated therapeutic to a subject in need thereof, comprising:
    administering to the subject, a sufficient amount of, a mixture of an anti-PEG antibody and a hydrogel, before, together with or after administering the PEGylated therapeutic;
    wherein,
    the hydrogel is hyaluronan (HA);
    the anti-PEG antibody and the hydrogel are present in the mixture in a ratio from about 1:1 to 1:100 (v/v); and
    at least two applications of the PEGylated therapeutic are administered to the subject, with each applications being about 1 hour to 1 week apart.

2. The method of claim 1, wherein the PEGylated therapeutic administered at each applications is different.

3. The method of claim 1, wherein the PEGylated therapeutic administered at each applications is the same.

4. The method of claim 1, wherein the PEGylated therapeutic and the mixture are administered to different sites of the subject.

5. The method of claim 1, wherein the PEGylated therapeutic and the mixture are administered to the subject via different routes.

6. The method of claim 1, wherein at least three applications of the PEGylated therapeutic are administered to the subject, with each applications being about 8 to 24 hours apart.

7. The method of claim 1, wherein the anti-PEG antibody is an IgM, IgG, humanized IgM or humanized IgG; and the HA has a molecular weight of about 20 kDa to 2,000 kDa.

8. The method of claim 7, wherein the HA has a molecular weight of about 1,500 kDa.

9. The method of claim 7, wherein the anti-PEG antibody and the HA are present n the mixture in a ratio of about 1:4 (v/v).

10. The method of claim 1, wherein the PEGylated therapeutic is suitable for treating cancer or ischemic disease.

11. The method of claim 10, wherein the ischemic disease is stroke, myocardial infarction (MI) or limb ischemia.

12. The method of claim 11, wherein the limb ischemia is any of critical limb ischemia, acute limb ischemia or Buerger's Disease.

13. The method of claim 10, wherein the cancer is any of breast cancer, cervical cancer, ovary cancer, endometrial cancer, melanoma, uveal melanoma, brain tumor, lung cancer, liver cancer, lymphoma, neuroepithelioma, kidney cancer, bladder cancer, pancreatic cancer, prostate cancer, stomach cancer, colon cancer, uterus cancer, hematopoietic tumors of lymphoid lineage, myeloid leukemia, thyroid cancer, thyroid follicular cancer, myelodysplastic syndrome (MDS), tumor of mesenchymal origin, teratcarcinoma, neuroblastoma, glioma, glioblastoma, keratoacanthomas, analplastic large cell lymphoma, esophageal squamous cell carcinoma, follicular dentritic cell carcinoma, intestinal cancer, muscle invasive cancer, seminal vesicle tumor, epidermal carcinoma, spleen cancer, head and neck cancer, stomach cancer, bone cancer, cancer of retina, biliary cancer, small bowel cancer, salivary gland cancer, uterine sarcoma, cancer of testicles, cancer of connective tissue, prostatic hypertrophy, myelodysplasia, Waldenstrom's macroglobulinemia, nasopharyngeal, neuroendocrine cancer, mesothelioma, angiosarcoma, Kaposi's sarcoma, oesophagogastric, fallopian tube cancer, peritoneal cancer, papillary serous mullerian cancer, malignant ascites, gastrointestinal stromal tumor (GIST), Li-Fraumeni syndrome or Von Hippel-Lindau syndrome (VHL).

14. The method of claim 13, wherein the hematopoietic tumors of lymphoid lineage may be any of leukemia, acute lymphocytic leukemia, chronic lymphocytic leukemia, B-cell lymphoma, Burkitt's lymphoma, multiple myeloma, Hodgkin's lymphoma, or Non-Hodgkin's lymphoma.

* * * * *